United States Patent
Bley et al.

(10) Patent No.: US 11,622,884 B2
(45) Date of Patent: Apr. 11, 2023

(54) OPHTHALMIC DELIVERY DEVICE AND OPHTHALMIC DRUG COMPOSITIONS

(71) Applicant: Oxular Limited, Oxford (GB)

(72) Inventors: Robert Steven Bley, Menlo Park, CA (US); Stanley R. Conston, San Carlos, CA (US); Ronald Yamamoto, San Francisco, CA (US)

(73) Assignee: Oxular Limited, Oxford (GB)

( * ) Notice: Subject to any disclaimer, the term of this patent is extended or adjusted under 35 U.S.C. 154(b) by 476 days.

(21) Appl. No.: 16/085,106

(22) PCT Filed: Mar. 16, 2017

(86) PCT No.: PCT/GB2017/050731
§ 371 (c)(1),
(2) Date: Sep. 14, 2018

(87) PCT Pub. No.: WO2017/158366
PCT Pub. Date: Sep. 21, 2017

(65) Prior Publication Data
US 2020/0330269 A1    Oct. 22, 2020

Related U.S. Application Data

(60) Provisional application No. 62/309,350, filed on Mar. 16, 2016.

(51) Int. Cl.
*A61F 9/00* (2006.01)
*A61K 9/16* (2006.01)
(Continued)

(52) U.S. Cl.
CPC .......... *A61F 9/0017* (2013.01); *A61K 9/0024* (2013.01); *A61K 9/0048* (2013.01);
(Continued)

(58) Field of Classification Search
CPC .... A61F 9/0017; A61F 9/0008; A61F 9/0026; A61F 9/00781; A61F 9/007;
(Continued)

(56) References Cited

U.S. PATENT DOCUMENTS

| 1,641,976 A | 9/1927 | Laurent |
| 3,890,971 A | 6/1975 | Leeson |

(Continued)

FOREIGN PATENT DOCUMENTS

| CN | 103327939 | 9/2013 |
| CN | 106492284 | 3/2017 |

(Continued)

OTHER PUBLICATIONS

Einmabl et al., "Evaluation of a Novel Biomaterial in the Suprachoroidal Space of the Rabbit Eye", IOVS, 2002, 43(5), pp. 1533-1539.
(Continued)

*Primary Examiner* — Kai H Weng
*Assistant Examiner* — Brandon W. Levy
(74) *Attorney, Agent, or Firm* — Armstrong Teasdale LLP

(57) ABSTRACT

The present invention provides a cannulation device for administering an active agent containing composition to the suprachoroidal space or supraciliary space. The invention provides methods of treatment of an ocular disease or condition accordingly. The invention also provides compositions for use in a method of treatment of an ocular disease or condition for delivery into the suprachoroidal space or supraciliary space.

27 Claims, 6 Drawing Sheets

(51) Int. Cl.

| | |
|---|---|
| *A61K 31/573* | (2006.01) |
| *A61K 9/00* | (2006.01) |
| *A61K 9/50* | (2006.01) |
| *A61K 9/70* | (2006.01) |
| *A61K 31/165* | (2006.01) |
| *A61K 31/192* | (2006.01) |
| *A61K 31/196* | (2006.01) |
| *A61K 31/407* | (2006.01) |
| *A61K 31/436* | (2006.01) |
| *A61K 35/28* | (2015.01) |
| *C07K 16/24* | (2006.01) |
| *C12N 15/113* | (2010.01) |
| *A61M 5/19* | (2006.01) |
| *A61M 5/315* | (2006.01) |
| *A61M 5/32* | (2006.01) |
| *A61M 5/20* | (2006.01) |

(52) U.S. Cl.
CPC .......... *A61K 9/0051* (2013.01); *A61K 9/1635* (2013.01); *A61K 9/1641* (2013.01); *A61K 9/1647* (2013.01); *A61K 9/1652* (2013.01); *A61K 9/5015* (2013.01); *A61K 9/5026* (2013.01); *A61K 9/5031* (2013.01); *A61K 9/5036* (2013.01); *A61K 9/5042* (2013.01); *A61K 9/5052* (2013.01); *A61K 9/5057* (2013.01); *A61K 9/70* (2013.01); *A61K 31/165* (2013.01); *A61K 31/192* (2013.01); *A61K 31/196* (2013.01); *A61K 31/407* (2013.01); *A61K 31/436* (2013.01); *A61K 31/573* (2013.01); *A61K 35/28* (2013.01); *A61M 5/19* (2013.01); *A61M 5/31596* (2013.01); *A61M 5/329* (2013.01); *C07K 16/241* (2013.01); *C12N 15/113* (2013.01); *A61M 2005/2026* (2013.01); *C12N 2310/14* (2013.01)

(58) Field of Classification Search
CPC ...... A61F 2250/0067; A61F 2250/0068; A61F 9/00; A61K 9/0024; A61K 9/0048; A61K 9/0051; A61K 9/1635; A61K 9/1641; A61K 9/1647; A61K 9/1652; A61K 9/5015; A61K 9/5026; A61K 9/5031; A61K 9/5036; A61K 9/5042; A61K 9/5052; A61K 9/5057; A61K 9/70; A61K 31/165; A61K 31/192; A61K 31/196; A61K 31/407; A61K 31/436; A61K 31/573; A61K 35/28; A61K 47/10; A61K 47/32; A61K 9/06; A61K 9/0019; A61K 9/5021; C07K 16/241; C12N 15/113; C12N 2310/14; A61P 9/12; A61P 25/00; A61P 27/02; A61P 29/00; A61P 31/00; A61P 43/00; A61M 2005/31598; A61M 2005/3267; A61M 5/178; A61M 31/002; A61M 2210/0612; A61M 5/2033; A61M 2005/206; A61M 5/3202; A61M 5/3204; A61M 5/3243; A61M 2005/2073; A61M 2005/208; A61M 5/31571; A61M 5/322; A61M 5/326; A61M 2005/202; A61M 5/3286; A61J 1/1406; A61J 1/201; A61J 1/2048; A61J 1/2055; A61J 1/2072; A61J 1/2089; A61J 1/2096; A61J 2200/10; A61B 2018/1425
See application file for complete search history.

(56) References Cited

U.S. PATENT DOCUMENTS

| | | | |
|---|---|---|---|
| 5,078,697 A | 1/1992 | Rammler | |
| 5,102,388 A | 4/1992 | Richmond | |
| 5,236,424 A * | 8/1993 | Imran | A61M 25/0074 604/48 |
| 5,250,031 A * | 10/1993 | Kaplan | A61M 5/3275 604/110 |
| 5,295,972 A | 3/1994 | Mischenko | |
| 5,358,489 A * | 10/1994 | Wyrick | A61M 5/2033 604/157 |
| 5,665,071 A | 9/1997 | Wyrick | |
| 5,957,897 A | 9/1999 | Jeffrey | |
| 6,409,706 B1 | 6/2002 | Loy | |
| 6,551,291 B1 | 4/2003 | de Juan et al. | |
| 2003/0057347 A1 | 3/2003 | Weiss | |
| 2004/0039337 A1 | 2/2004 | Letzing | |
| 2004/0078006 A1 | 4/2004 | Bills | |
| 2005/0070848 A1 | 3/2005 | Kim | |
| 2006/0141049 A1 | 6/2006 | Lyons et al. | |
| 2007/0202186 A1 | 8/2007 | Yamamoto et al. | |
| 2008/0033351 A1 | 2/2008 | Trogden et al. | |
| 2008/0234637 A1 | 9/2008 | McConnell et al. | |
| 2009/0036827 A1 | 2/2009 | Cazzini | |
| 2009/0148527 A1 | 6/2009 | Robinson et al. | |
| 2010/0104654 A1 | 4/2010 | Robinson et al. | |
| 2010/0249721 A1 * | 9/2010 | Guillermo | A61M 5/3155 604/246 |
| 2010/0305514 A1 * | 12/2010 | Valenti | A61F 9/0017 604/239 |
| 2011/0238075 A1 | 9/2011 | Clauson et al. | |
| 2012/0271272 A1 * | 10/2012 | Hammack | A61F 9/00736 604/257 |
| 2013/0096534 A1 | 4/2013 | Orilla et al. | |
| 2013/0202186 A1 | 8/2013 | Fang et al. | |
| 2013/0296825 A1 | 11/2013 | Lerner | |
| 2013/0345618 A1 | 12/2013 | Auld et al. | |
| 2014/0257200 A1 * | 9/2014 | Auerbach | A61M 5/3272 604/263 |
| 2015/0038905 A1 | 2/2015 | Andino et al. | |
| 2015/0223977 A1 * | 8/2015 | Oberkircher | A61F 9/0017 604/521 |
| 2015/0273161 A1 * | 10/2015 | Bengtsson | A61M 5/326 604/198 |
| 2015/0351958 A1 | 12/2015 | Contiliano et al. | |
| 2017/0224534 A1 | 8/2017 | Andino et al. | |

FOREIGN PATENT DOCUMENTS

| | | |
|---|---|---|
| DE | 102010048085 | 4/2012 |
| EP | 1450884 | 9/2004 |
| EP | 2248494 | 11/2010 |
| GB | 2531910 | 5/2016 |
| GB | 2536517 | 9/2016 |
| JP | H10-507239 | 8/1996 |
| JP | H8-507239 | 8/1998 |
| WO | 2004094823 | 11/2004 |
| WO | 2005070490 | 8/2005 |
| WO | 2005107845 | 11/2005 |
| WO | 2006044029 | 4/2006 |
| WO | 2007100745 | 11/2007 |
| WO | 2009010591 | 1/2009 |
| WO | 2009/089409 | 7/2009 |
| WO | 2010003011 | 1/2010 |
| WO | 2010126833 | 11/2010 |
| WO | 2010147661 | 12/2010 |
| WO | 2011117592 | 9/2011 |
| WO | 2012051575 | 4/2012 |
| WO | 2012059449 | 5/2012 |
| WO | 2012115911 | 8/2012 |
| WO | 2013/028936 | 2/2013 |
| WO | 2013/151904 | 10/2013 |
| WO | 2013188595 | 12/2013 |
| WO | 2016/042163 | 3/2016 |

(56) References Cited

FOREIGN PATENT DOCUMENTS

| WO | 2016040635 | 3/2016 |
| WO | 2016042162 | 3/2016 |
| WO | 2016159999 | 10/2016 |

OTHER PUBLICATIONS

Notice of Allowance dated Jun. 25, 2021 in related U.S. Appl. No. 15/760,717.
Non-Final Office Action dated Aug. 28, 2020 in related U.S. Appl. No. 15/760,717.
Notice of Allowance dated Mar. 19, 2021 in related U.S. Appl. No. 15/760,717.
Notice of Allowance dated Apr. 26, 2021 in related U.S. Appl. No. 15/512,130.
Office Action dated Apr. 8, 2019 received in related U.S. Appl. No. 15/512,130.
Non-Final Office Action dated Nov. 27, 2020 in related U.S. Appl. No. 15/512,130.
Final Office Action dated Oct. 28, 2019 in related U.S. Appl. No. 15/512,130.
Non-Final Office Action dated Dec. 12, 2022 in related U.S. Appl. No. 16/085,083.

* cited by examiner

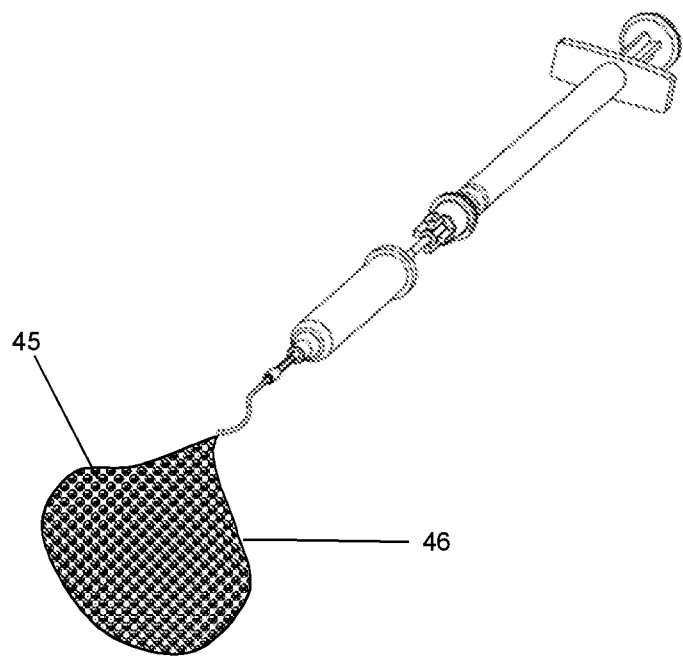
Fig. 10
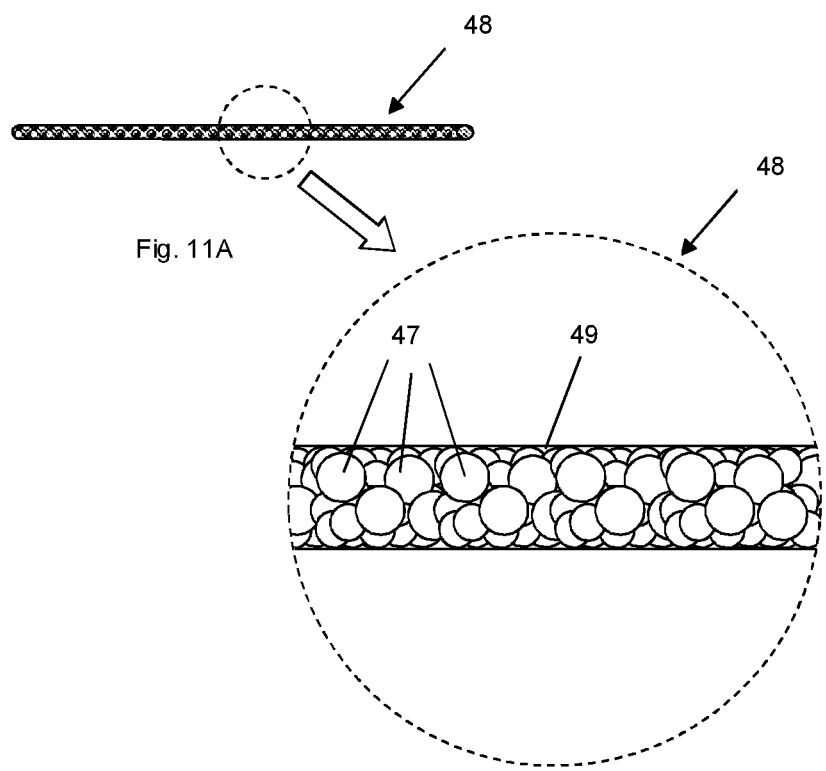
Fig. 11A
Fig. 11B

OPHTHALMIC DELIVERY DEVICE AND OPHTHALMIC DRUG COMPOSITIONS

CROSS REFERENCE TO OTHER APPLICATIONS

This application claims priority of U.S. Provisional Application No. 62/309,350, filed 16 Mar. 2016. The following patent applications are incorporated by reference: PCT/EP2015/071520, PCT/EP2015/071522.

BACKGROUND OF INVENTION

Due to the unique anatomy and physiology of the eye, multiple barriers exist that prevent significant transport of drugs to ocular tissues. The blood vessels of the eye have restricted permeability due to the blood-ocular barriers that regulate intraocular fluid. Due to these blood-ocular barriers, systemically administered drugs do not reach significant concentration in ocular tissues. Drugs in topical drops administered to the corneal surface are mostly washed out by tears into the naso-lacrimal duct. While in the tear film, drugs have limited time to penetrate the cornea to reach the intraocular space. Some drugs may be delivered to the front, anterior portion of the eye by drops, but reaching significant therapeutic concentrations in the posterior portion of the eye and the retina is generally not achieved with topical methods of administration.

Many diseases that result in visual loss involve the posterior retina where color vision and reading occur. To treat the posterior portion of the eye and the posterior retina typically drugs are injected into the eye. Sub-conjunctival injections are used to place a drug depot under the outer layer of the eye, however the very high lymphatic flow in the conjunctiva leads to rapid transport of the drug away from the eye. Sub-conjunctival injections are typically not effective to achieving high drug levels in the posterior portion of the eye.

Sub-Tenon's injections are sometimes used to place the drug under the conjunctiva and Tenon's capsule of the eye in a more posterior location to deliver drug to the posterior region of the eye. Sub-Tenon's injections have been demonstrated to be useful for the administration of steroids, however many drugs do not achieve significant drug levels in the retinal tissues from sub-Tenon's injection. The tip of the injection needle is placed deep into the posterior shell of the eye where the tip of the needle cannot be directly observed. The technique requires experience and careful technique to avoid physical injury to the eye or misplacement of drug.

Intravitreal injections are given to place drug directly into the vitreous chamber, and typically require a smaller quantity of drug as compared to sub-Tenon's injections. The half-life of the drug is limited due to the fluid in the vitreous which continuously moves forward toward the anterior chamber. This vitreous flow washes out the drug over time and contacts the drug to other tissues of the eye in the flow path. Intravitreally administered drugs such as steroids are associated with complications of cataract progression due to drug exposure to the lens and increased intraocular pressure from drug exposure to the trabecular meshwork during anterior flow from the vitreous chamber.

The suprachoroidal space between the choroid and sclera and the supraciliary space between the ciliary body and sclera are more difficult to locate but also can be used for the injection of drugs. Unlike intravitreal injections, the fluid in the suprachoroidal space and supraciliary space flows posteriorly. This flow may assist drugs injected into the suprachoroidal space or the supraciliary space to reach the posterior tissues and posterior retina. Small drug particle sizes are ideal for migration in the suprachoroidal space or supraciliary space, however small drug particles release drug at a much faster rate thereby reducing the longevity of the drug treatment.

One potential problem with all injections of drug into the eye beneath the sclera is increased intraocular pressure (IOP) caused by the additional volume introduced into the eye. The increased IOP may cause pain and potential damage to the optic nerve. For highly active drugs a small injection volume may be used without significant acute IOP increase, for example 0.05 ml of anti-VEGF drugs. However, for larger volumes such as 0.1 ml with steroids, IOP increase may be significant and may cause an acute period of pain and loss of vision.

SUMMARY OF THE INVENTION

In keeping with the foregoing discussion, the present invention provides a device designed for the minimally invasive insertion or placement of a flexible cannula into the suprachoroidal space or supraciliary space of an eye for the purpose of administering an active agent containing material. The cannula comprises an elongated tubular element which is placed into the suprachoroidal space or supraciliary space by passage through the lumen of a needle or trocar. A surgical instrument with a sharpened distal tip to insert a cannula is often described as a trocar, which is used interchangeably with the term "needle" in the present application. The invention is a cannulation device which incorporates a needle or trocar, a flexible cannula and a mechanism to facilitate one handed insertion of the cannula into the suprachoroidal space or supraciliary space.

The cannulation device comprises an elongated barrel with a hollow needle at the distal end, where the lumen of the needle serves as a reservoir for at least a portion of the flexible cannula, and a plunger with a force element such as a spring or gas reservoir that provides a force to the cannula to advance or deploy the cannula from the distal end of the needle. The distal end of the cannula is sized with a diameter less than or equal to the inner diameter of the needle lumen. In one embodiment, the deployment force is activated simultaneous with or immediately after advancement of the needle tip into tissue.

In one embodiment, the cannulation device also comprises a distal element comprising a tissue interface with a distal seal secured to the distal end of the cannulation device thereby sealing the needle lumen during application of the deployment force. The distal seal is penetrable or deformable by the distal tip of the needle by the application of pressure on the tissue surface with the distal end of the cannulation device and the penetrated distal element becomes slidable on the needle to allow advancement of the needle into tissue. Penetration of the distal seal opens a path for advancement of the cannula from the distal end of the needle. The force element of the cannulation device is activated prior to or simultaneous with penetration of the distal seal by the needle and advancement of the needle tip into tissues, thereby enabling simple one-handed operation of the cannulation device to administer the cannula to the suprachoroidal space or supraciliary space of an eye.

In one embodiment, the distal tip of the needle is curved or incorporates an inner deflecting element in the needle lumen to direct the cannula at an angle from the long axis of the needle during delivery of the flexible cannula. In one embodiment, the cannula is directed at an angle from the long axis of the needle during deployment in a posterior direction. In one embodiment, the cannula provides a fluid connection through the cannulation device to enable delivery of a flowable material for administration such as an active agent containing composition through the lumen of the cannula into a tissue space such as the suprachoroidal space or supraciliary space. In one embodiment, the cannulation device contains a reservoir of material for administration which may be delivered through the lumen of the cannula into the tissue space such as the suprachoroidal or supraciliary space. In one embodiment, the cannulation device contains a reservoir of material for administration which may be delivered through the lumen of the cannula into the tissue space such as the suprachoroidal or supraciliary space where the material for administration is a semisolid composition comprising a plurality of drug containing particles and an excipient. In one embodiment, the cannulation device contains a reservoir to contain a material for administration which may be delivered through the lumen of the cannula into the tissue space such as the suprachoroidal or supraciliary space where the material for administration consists of a plurality of drug containing particles dispersed in one or more excipients.

These and other aspects of the invention will be made apparent from consideration of the following detailed description in conjunction with the accompanying drawing figures.

BRIEF DESCRIPTION OF THE DRAWINGS

FIG. 10 depicts a delivery device expelling a semi-solid composition for administration.

FIG. 11A depicts a solid or semi-solid composition for administration shaped as an elongated body.

FIG. 11 B depicts a magnified portion of FIG. 11A.

DESCRIPTION OF THE INVENTION

Figure 1A:
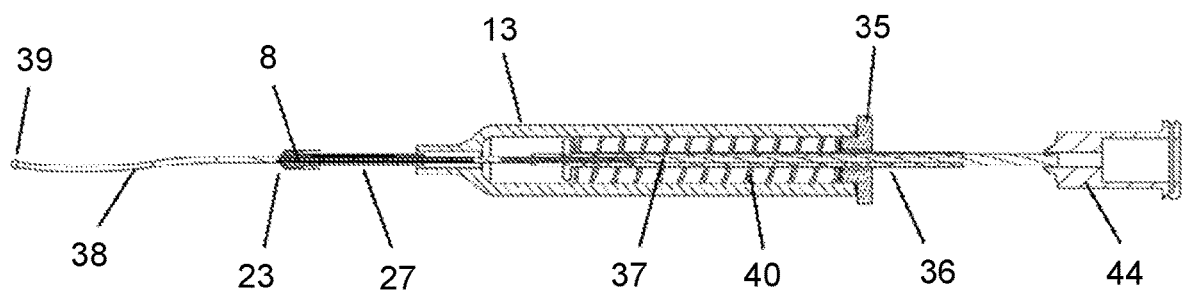
FIG. 1A depicts one embodiment of a cannulation device for deploying a flexible cannula into a tissue space of an eye and FIG.1B depicts another embodiment of a cannulation device for deploying a flexible cannula into a tissue space of an eye.

The invention is a device that provides minimally invasive cannulation of the suprachoroidal space or supraciliary space. Subsequent to the cannulation, the device may be used to deliver a material for administration such as an active agent containing composition into the space through the cannula. In particular, the material for administration is a fluid, suspension or semisolid active agent containing composition. The active agent may be a substance that provides a therapeutic or diagnostic effect for treatment of an eye. The active agent may comprise a drug, a diagnostic agent, gene therapy agents, therapeutic cells or means for physical tissue repair.

Placement of a cannula into the suprachoroidal space or supraciliary space of an eye provides a means to deliver an active agent containing composition to a location in the space distant from the site of tissue penetration to access the site. The cannulation device of the present invention allows an active agent containing composition to be administered and directed toward the posterior retina from an anterior tissue access site such as the pars plana. The cannulation device may also be designed and used to deliver an active agent containing composition to a specific site in the eye to treat a local condition such as a tumor.

The cannulation device comprises an elongated barrel with a hollow needle at the distal end and a cannula comprising an elongated tubular element, where the lumen of the needle serves as the reservoir for at least a portion of the tubular element. The cannulation device further comprises a force element such as a spring or gas reservoir that provides a force to advance or deploy the cannula through the lumen and out from the distal end of the needle into a tissue space. The force element may be mechanically coupled to the cannula by a push rod or plunger between the push rod and the cannula. Alternatively, the end of the force element may be directly mated to a section of the cannula. The force element, force element plunger or force element push rod may be connected to the cannula by an interfacing sleeve or other forms of attachment. Prior to use, the distal portion of the cannula is within the needle and body of the cannulation device. The cannula is configured to extend from the distal tip of the needle once deployed by the force element. The cannula has a length to allow extension of the distal end of the cannula from the distal tip of the needle when deployed. The cannula is configured with a deployed length from the distal tip of the needle to the intended site of delivery of an active agent containing composition. In one embodiment, the length of the cannula from the distal tip of the needle in the deployed state ranges from 2 to 15 mm. A very short length deployed cannula is useful for directing the material for administration in a preferred direction from the needle penetration site. In particular, a deployed length from the distal tip of the needle in the range of 6 to 12 mm allows the cannula to be introduced in the eye at the pars plana to avoid potential damage to the retina, and place the distal tip of the cannula near the posterior retina to deliver a material for administration to the most visually important portion of the eye.

The cannula is sized with a diameter less than or equal to the inner diameter of the needle lumen and is slidably disposed in the needle lumen. The cannula has a proximal end to receive the active agent containing composition and a distal tip to deliver the active agent containing composition. In one embodiment, the distal tip of the cannula is configured with a rounded profile to provide for an atraumatic tip for entering the tissues. The rounded profile may be created by thermal treatment of the distal tip of the cannula, by directly molding the cannula to include the atraumatic tip, or by application of a material to the distal tip. The applied material may be the same as the cannula material in a solvent dispersion, a different material than the cannula material in a solvent dispersion or an adhesive. The atraumatic distal tip may also be formed as a separate component and attached to the distal end of the cannula by thermal or adhesive means. In one embodiment, the material for administration such as an active agent containing composition is directed into the proximal end of the cannula from a connector, such as a Luer connector or an injection port in communication with the proximal end of the cannula. The connector or injection port may be located on the device or attached to the device. In one embodiment, the material for administration such as an active agent containing composition is located in a reservoir in the body of the cannulation device and administered through the lumen of the cannula by the user. The size of the reservoir may be configured appropriately for the volume of material to be delivered. The reservoir may be sized for delivery volumes ranging from, for example, 0.1 microliters to 500 microliters. The material for administration may be delivered manually by a plunger or by actuation of a force element acting on a plunger to move the plunger in the reservoir and provide a delivery force on the material for administration. For small volumes of administration, the lumen of the cannula may also act as a reservoir for the active agent containing composition. For small volumes of administration, the lumen of the cannula may also act as a reservoir for the active agent containing composition and a plunger may be configured to move distally in the lumen of the cannula to provide a delivery force on the material for administration.

In one embodiment, the deployment force is activated immediately after or simultaneous with advancement of the needle tip into tissue. The activation may be performed by release of the force element by the user or by a mechanism at the distal tip of the device.

In one embodiment, the cannulation device also comprises a distal element which functions as a tissue interface with a distal seal secured to the distal end of the cannulation device thereby sealing the needle lumen during application of the deployment force. The distal seal is penetrable by the distal tip of the needle by the application of pressure on the tissue surface with the distal end of the cannulation device and the penetrated distal element becomes slidable on the needle to allow advancement of the needle into tissue. Penetration of the distal seal opens a path for delivery of the cannula from the distal end of the needle. The cannulation device with a force element is activated prior to or simultaneous with penetration of the distal seal by the needle and advancement of the needle tip into tissues. The resulting self-actuating deployment mechanism insures opening of the delivery path for the cannula immediately when the needle is placed in tissue, regardless of the orientation and speed of needle insertion. The self-actuation mechanism enables simple one-handed operation of the cannulation device to administer the cannula to the suprachoroidal space or supraciliary space of an eye.

In one embodiment, the distal element comprises a tissue interface and distal seal mounted on a tubular distal housing. The tubular distal housing is fit to the exterior of the needle and may be sealed to the surface of the needle at some point along its length. In one embodiment the housing may be sealed by means of an elastomeric element which is compressed between the housing and the needle. The elastomeric element may therefore be annular. In one embodiment, the elastomeric element may be compressed between the housing and the body of the device. The elastomeric element may reside at or near the proximal end of the housing. In one embodiment the elastomeric element serves as a seal between the housing and the needle. In one embodiment the elastomeric element serves as a frictional element or component which limits the housing travel in the proximal direction to thereby apply a force against the tissue surface by the tissue interface as the needle penetrates the tissues. In some embodiments, the distal element comprises a tissue interface and a distal seal and is slidably attached to the exterior of the needle without a distal housing.

The distal element, which comprises a tissue interface with a distal seal, or a tissue interface with a distal seal and an attached housing, is attached to the distal tip of the needle but is not freely movable or slidable proximally from the end of the needle due to the distal seal. After the cannulation device is primed or activated for use, the cannula is under a deployment force from the force element but cannot move through the distal seal. The tissue interface is placed on the surface of the eye and the device is manually advanced, thereby forcing the needle through the distal seal and then through the external surface of the eye into underlying tissues. The distal element, after penetration of the distal seal, becomes proximally slidable from the end of the needle to retain the tissue interface on or near the surface of the eye during advancement of the needle into tissue. When the distal tip of the needle penetrates through the distal seal, the source of force immediately allows for deployment of the cannula from the needle tip and into the tissue space.

In one embodiment the tissue interface and distal seal is secured to a housing disposed about the needle. The housing may be comprised of a cylindrical element which is secured to the distal end of the body of the device at the proximal end of the housing. The housing may contain collapsible, distortable or deformable elements which allow the distal end of the housing to retract slidably along the needle, which in turn allows the needle tip to penetrate the distal seal. In some embodiments the distal element is secured to the distal tip of the needle through other means.

In one embodiment, the cannulation device comprises an elongated barrel with a hollow needle at the distal end, a cannula to be deployed residing at least partially in the needle lumen and a force element such as a spring or pressurized gas (15) source mechanically coupled to the cannula to deploy the cannula. The deployment of the cannula may be actuated either manually by activating the force element or by action of the needle penetration into tissues to place the cannula in a tissue space when the distal tip of the device reaches the space.

In one embodiment, operation of the device mechanism opens the path for the cannula to deploy from the tip of the needle immediately upon penetration of the needle through a distal seal which occurs just prior to the entry of the needle into the target tissue. Since the cannula is under a deployment force prior to or simultaneous with penetration of the distal seal by the needle tip, the deployment is triggered solely by placement and subsequent advancement of the needle through the tissue interface. This allows precise and automatic control of the timing of the deployment action solely due to the needle tip entering the target tissue. The resultant self-actuated mechanism obviates the need for a separate control mechanism, for example a valve or trigger on the body of the cannulation device, and hence allows for deployment of the cannula without the need for special positioning of the fingers or the use of the second hand. The cannulation device thereby enables cannulation to be performed with a single hand, allowing the other hand of the physician to stabilize the eye or perform other actions to facilitate the procedure. The self-actuating cannulation mechanism also eliminates the need for the user to determine when to begin deployment which is especially useful when the target tissue space is difficult to locate due to small target size, lack of visualization and anatomic variability such as the suprachoroidal space or supraciliary space.

The cannulation device allows precise control of the position of the needle by the user during use. The needle is fixed to the body of the device to allow direct control of the distal tip of the needle when the device is held. Since the deployment force is provided by the force element, the cannula does not have to be held or advanced by the hand holding the device, allowing the device to be held and used in a natural, highly controllable position such as with a writing instrument or scalpel. Generally, the needle is arranged parallel to the elongated body or barrel of the device.

Once the path from the distal end of the needle lumen is opened by needle penetration of the distal seal and insertion into the eye, the cannula cannot extend or deploy from the distal tip of the needle until a space to accept the cannula is reached by the distal end of the needle. Scleral tissue in particular is very resilient and effectively seals the needle tip during passage of the needle tip to the suprachoroidal or supraciliary space, hence the unique properties of the sclera do not allow for the cannula to enter the sclera. Once an underlying space such as the suprachoroidal space or the supraciliary space is reached by the needle tip, the cannula is able to advance out of the needle and be deployed in the space. By this mechanism the cannula is directed to a location that can accept the cannula at the distal tip of the needle. Subsequent to the deployment of the cannula, a material for administration such as an active agent containing composition may be delivered through the lumen of the cannula to the eye.

The flexible cannula of the cannulation device is designed with the appropriate mechanical properties with suitable flexural modulus to allow the cannula to bend to advance into the suprachoroidal space or supraciliary space and with a suitable axial compressive stiffness to allow advancement of the cannula into the space by the deployment force on a proximal segment of the cannula. The mechanical properties can be suitably tailored by the selection of the cannula material and the cannula dimensions. In addition, the cannula may have features to tailor the mechanical properties. A stiffening element such as a wire may be placed in the lumen or wall of the cannula to increase axial buckling strength. The distal tip of the cannula may also be reinforced for example with a coil or coating to tailor both the buckling strength and flexibility of the distal portion of the cannula. The coil can be fabricated from metal or high modulus polymers and placed on the outer surface of the cannula, the inner surface of the cannula or within the wall of the cannula. The cannula may be fabricated from polymers such as polyether block amide (PEBA), polyamide, perfluoroalkoxy polymer, fluorinated ethylenepropylene polymer, ethylenetetrafluoroethylene copolymer, ethylene chlorotrifluoroethylene copolymer polystyrene, polytetrafluoroethylene, polyvinylidene, polyethylene, polypropylene, polyethylene-propylene block copolymers, polyurethane, polyethylene terephthalate, polydimethylsiloxane, polyvinylchloride, polyetherimide and polyimide. For some applications, the cannula may be fabricated from a flexible metal such as a nickel titanium super elastic alloy (nitinol).

The delivery of the material for administration may be aided by the tissue interface. The tissue interface may optionally apply a force to the surface of the eye to aid sealing of the needle tract at the surface of the eye to prevent reflux of the material for administration. With an appropriate needle length and orientation, the device may be used to deploy a cannula and deliver materials for administration into the sub-conjunctival space, suprachoroidal space, supraciliary space and sub-retinal space, the vitreous cavity, or the anterior chamber.

The needle comprises a stiff material, with a diameter to allow the cannula to pass through the lumen of the needle, typically in the range of 20 gauge to 40 gauge (for example, less than 0.91 mm outer diameter/0.6 mm inner diameter), where the length of the needle is suitable to reach the intended tissue space. The needle is fixed to the body or barrel of the device and generally does not slide or move in relation to the body to provide precise control of needle depth during penetration of tissues.

The distal tip of the needle may be beveled or sharpened to aid penetration. The bevel angle may be designed to facilitate entry into a specific target. For example, a short bevel of 18 degree bevel angle may be used to cannulate into narrower spaces such as the subconjunctival or sub-Tenon's space. A medium bevel needle of 15 degree bevel angle may be used to cannulate into spaces such as the suprachoroidal or supraciliary space. Longer bevels, such as 12 degree bevel angle may be used to cannulate into the anterior or posterior chambers.

In one embodiment, the distal element is designed with a complementary bevel in a lumen of the distal element to provide close apposition of the distal seal to the needle bevel. The bevel of the needle is in alignment with the bevel in a lumen of the distal element. The most distal portion of the distal element may be flat or beveled to aid orientation of the needle during tissue penetration to aid reaching certain tissue spaces. For example, a beveled tissue contacting surface of the distal element may aid targeting of cannulation into the tissue targets with less depth such as the subconjunctival space, sub-Tenon's space and in some regions of the suprachoroidal space. The angle of the tissue contacting surface of the distal element may range from 90 degrees from the axis of the distal element for perpendicular insertion, to 45 degrees from the axis.

In some applications of the invention, it may be desired for the distal tip of the needle to direct the cannula at an angle from the long axis of the needle. Such a design reduces force of the cannula on the underlying tissues such as the ciliary body or choroid and may also be used to direct the cannula in a desired direction such as toward the posterior region of the suprachoroidal space near the macular region of the retina. The distal tip of the needle may be curved in the range of 5 to 60 degrees to direct the cannula. The distal tip of the needle may also have an inner deflecting element in the lumen of the needle in the region of the bevel of the needle. The inner deflecting element may be a protrusion, a sloped surface or a ramp to direct the cannula away from the long axis of the needle. The inner deflecting element may be located along the entire length of the needle bevel or in a discrete location from the proximal end of the bevel. In one embodiment, the inner deflecting element is located at a position from the distal end of the bevel, 20% to 80% of the length of the needle bevel, 25% to 75% of the length of the needle bevel or 30% to 60% of the length of the needle bevel. The body of the device may incorporate a label or indicator to provide the user with the orientation to the direction of the cannulation, for instance a notation of the orientation of the needle bevel or the direction in which a deflection element will deflect the cannula.

The needle may be constructed from a metal, ceramic, high modulus polymer or glass. The length of the needle in tissue is selected to match the target location for the cannulation and the variation in target location due to anatomical variability. The effective full length of the needle is the length of the needle distal tip to the distal surface of the tissue interface, when the distal element has achieved full proximal travel. The distal element moves slidably on the needle during needle advancement into tissue, allowing for progressive increase in the length of needle protruding through the distal element during advancement into tissue. The cannula is deployed automatically once the needle reaches the appropriate location which may be less than the effective full length of the needle. The release of force and resultant time for deployment occurs quickly, in approximately 0.1 to 3 seconds depending on the deployed length of the cannula and the amount of force from the force element. The time for deployment may also be controlled by a damping or frictional mechanism coupled to advancement of the cannula to limit the speed of cannula advancement or deployment. The release of force from the force element communicates to the physician with both visible and tactile feedback that there is no need for additional advancement of the needle. The rapid deployment event gives the physician sufficient time to halt needle advancement, resulting in an effective variable needle length to accommodate patient to patient differences in tissue thickness. The variable needle length and self-actuation of deployment is especially useful for cannulation into spaces that are not normally open, such as the subconjunctival space, sub-Tenon's space, suprachoroidal space and supraciliary space. For the subconjunctival space and sub-Tenon's space the needle effective full length is in the range of 0.35 mm to 2 mm depending on the angle of needle insertion. For the suprachoroidal space and supraciliary space, the needle effective full length is in the range of 1 mm to 4 mm depending on the angle of insertion. For the vitreous cavity, the needle effective full length is in the range of 10 to 15 mm. The effective full needle length may, for example, be 0.3 mm to 3 mm, 0.35 to 2 mm, 1 mm to 4 mm, 10 to 15 mm.

In one embodiment, the distal element applies a distally directed sealing force against the tissue surface to maintain a seal on the surface of the eye. The sealing force is designed to be sufficient to seal the flow of the material for administration from the needle track during administration of the delivery material. The sealing force is minimized to prevent compression of the tissues of a normally closed space or nearly closed space such as the suprachoroidal or supraciliary space at the site of needle penetration that would prevent cannulation into the space or increasing the intraocular pressure that would restrict movement of the material for administration into the normally closed or nearly closed space. In one embodiment, the distal element maintains contact with the tissue surface but does not apply a distally directed sealing force against the tissue surface to maintain a seal on the surface of the eye. In one embodiment, the distal element contacts the surface of the eye during penetration of the distal seal of the distal element by the distal tip of the needle but does not maintain contact with the surface of the eye after needle penetration through the distal seal and into ocular tissue. The tissue interface and distal seal may comprise a soft polymer, rubber or other material that allows needle penetration without coring of the material. The tissue interface and distal seal material may be selected to provide compliance to the surface of the eye during insertion of the needle into ocular tissue and also to seal the deployment pathway from the needle until the needle is advanced through the distal seal. Once the needle penetrates the distal seal, the needle is advanced through the outer ocular tissues to reach the desired cannulation site. The tissue interface and distal seal remain on the surface of the eye. The distal seal is sufficiently resilient to prevent rupture by the cannula under deployment force prior to advancement of the needle through the distal seal. The portion of the distal seal in the path of the needle is also sufficiently thin to allow penetration by the needle without undue application of force. The distal seal is typically in the range of 250 to 1500 microns in thickness in the region that is penetrated by the needle.

In one embodiment a sealing force is provided by a compressible or collapsible element between the body of the device and the proximal end of the distal element or distal housing. In one embodiment, the tissue interface provides a sealing force by compression of the tissue interface or elastically compressible elements in the distal element. In one embodiment, the distal element is configured to allow an elastic reduction in length during needle advancement to apply a sealing force. In one embodiment, a friction element disposed in or about the distal element increases the force required to move the distal element proximally thereby promoting contact of the tissue interface with the surface of the eye and maintaining a seal against the eye surface during needle advancement. The friction of the distal element against the needle may be tailored in relation to the proximal movement of the distal element during needle advancement. An increase in friction may be obtained by increased contact or surface texture between the distal element and the external surface of the needle or through a decrease in the durometer of the distal element in order to tailor the amount of force applied by the tissue interface during proximal travel of the interface along the needle length. The friction may be varied along the path of travel of the distal element along the needle. High friction may be provided during the initial path of travel of the distal element to promote contact of the tissue interface to the surface of the eye during initial insertion of the needle into ocular tissues, the friction may be reduced after a length of the needle corresponding to the length of the needle bevel is inserted into ocular tissue. The length of travel of the distal element under the influence of the region of high friction is in the range of 0.3 mm to 2 mm.

In one embodiment, the distal element is attached to the body of the device by one or more collapsible elements. The collapsible element is configured to not allow an increase in length to prevent the distal seal from being displaced from the tip of the needle due to the deployment force applied to the cannula prior to penetration of the distal seal. The collapsible element allows a reduction in length, thereby allowing proximal travel of the distal element during advancement of the needle into tissues. In one embodiment, the collapsible element comprises one or more elongated struts that may deform, bend or fold away from the needle during proximal travel of the distal element. In one embodiment, the collapsible element comprises a section of tubing concentric to the needle that has been cut to form openings along the axial length of the tubing to form collapsible struts. The shape and configuration of the collapsible struts may be tailored to provide a desired force-displacement characteristic of the collapsible element. The force versus displacement may be linear or non-linear. In one embodiment the collapsible element provides a sealing force which transitions from an increasing spring like force per unit displacement to a constant force independent of displacement to keep the tissue interface and distal seal in sealing contact to the eye surface without undue application of force with further needle advancement into the eye. Application of force above 80 to 100 grams-force may limit the ability of the cannula to enter a closed space such as the suprachoroidal or supraciliary space. In one embodiment, the tissue interface applies a sealing force in the range of 40 to 80 gram force. The transition to a constant force is designed to occur after a length of the needle bevel is inserted into ocular tissue, corresponding to a compression or collapse of the collapsible element of 0.3 mm to 2 mm. In one embodiment the collapsible element provides for contact of the tissue interface to the surface of the eye during initial insertion of the needle into ocular tissue, but collapses to provide little or no resistance to proximal movement of the distal element along the needle after the bevel of the needle is fully inserted into tissue. The collapsible element may be assembled from components in a tubelike configuration or alternatively cut from a segment of tubing such as a laser machined nickel titanium alloy (e.g. Nitinol) tube or a polyimide tube. The collapsible element may be disposed between the elongate body and the distal element, such as between the barrel and the housing of the distal element (if present). The collapsible element may be fixed to the body of the device and to the distal element such that the distal element is proximally slidable on the needle but will not travel distally from its initial position.

In some embodiments the tissue interface provides a sealing function. The sealing force provided by the tissue interface is within a range to provide sealing of the needle tract, but less than the force that would close the tissue space to impede movement of the material for administration into the space. A tissue interface with a tissue contacting surface area in the range of 0.45 to 5.07 mm$^2$ is suitable for sealing of the needle tract. Suitable materials for the tissue interface and distal seal include, but are not limited to, natural rubbers, silicone rubbers and thermoplastic elastomers such as polyurethanes. The stiffness of the rubber or elastomer may be selected to provide the appropriate combination of conformance to the tissue surface and sealing of the lumen of the distal end of the needle. The selection of the material of the tissue interface may also minimize the sealing force that might impede movement of the cannula into the tissue space. The rubber or elastomer must also be capable of penetration or deformation by the distal tip of the needle to trigger release of the cannula. Rubbers or elastomers with a Shore A durometer of 10 to 70, 10 to 50 or 10 to 30 are suitable for use as the sealing element. Suitable materials for a distal housing include, but are not limited to, polypropylene, polyethylene, polycarbonate, polysulfone, polyeheretherketone, acrylonitrile butadiene styrene, polystyrene, polyamide, and polyurethanes. Suitable materials for a distal collapsible element include, but are not limited to, stainless steel, spring temper steel, super-elastic nickel titanium alloys, cobalt chrome alloys, oil-tempered chrome silicon, polyimide, and polyetherimide.

In one embodiment, the body or barrel of the device contains the reservoir and provides an external surface for holding the device during use. The reservoir may comprise a tubular cylinder attached on the distal end to the proximal end of the needle, with a plunger slidably disposed in the lumen of the tubular body. The reservoir may also provide for insertion of a cartridge containing the material for administration where a plunger of the device moves a slidable seal in the proximal end of the cartridge to deliver the material. The body of the device may be fabricated from a variety of thermoplastic materials suitable for medical use such as polypropylene, polyamide, polycarbonate, polysulfone, polyethylene, cyclic polyolefins, polystyrene and polymethylmethacryate. The body may incorporate external features such as textures or finger indentations to allow a user to more ergonomically grip and use the device. The body may incorporate index or measurement markings to provide an indication of the amount of material being delivered. The body may incorporate transparent materials or a section of transparent material to allow the visualization of the material for administration in the reservoir or movement of the plunger to visually indicate the delivery event. The plunger may have markings to aid visualization of reservoir loading and release of the material for administration. The body of the device may incorporate a label or indicator to provide the user with the orientation to the direction of the cannulation, for instance a notation of the orientation of the needle bevel or the direction in which a deflection element will deflect the distal tip of the cannula during deployment.

In embodiments of the invention, the device comprises a means for providing a deployment force to the cannula. In embodiments of the invention, the device comprises a means for providing a force to deliver the material for administration from a reservoir within the device. The means as described herein could be, for example, a compressible reservoir or levers that can be "squeezed" or compressed by a user (directly or indirectly) to effect deployment of the cannula or delivery of the material for administration. Alternatively, in one embodiment, the means is a mechanism with a biasing means or force element (such as a compression spring or a pressurized gas (15)).

The device may be disposable and/or for single use. Alternatively, the device may be reusable.

In some embodiments, the distal seal acts to prevent escape of the cannula from the needle when the device is primed by activation of the force element prior to contact of the needle with the eye. This can be achieved by a seal between the needle lumen and the outside of the device. This seal may be achieved by the seal being in direct contact with the needle tip or may be achieved by using a distal element housing that is suitably sized to provide a seal around the needle shaft when placed over the needle tip. For example, the outer diameter of the needle may be complimentary to the inner diameter of the housing to provide a seal. In embodiments of the invention, the seal may only block enough of the needle lumen so as to prevent the cannula from being deployed until the seal is moved proximally, thereby fully exposing the opening of the lumen. In such embodiments the distal seal is a virtual seal and not covering the entirety of the needle lumen at the distal end of the needle. Hence the seal may comprise deformable protrusions (57) that extend into the lumen at the distal end of the needle or that extend into a distal projection of the lumen from the distal end that would be sufficient to prevent deployment of the cannula. Needle penetration through such embodiments of the distal seal may be achieved by deformation of the protrusions (57) by the distal tip of the needle as it passes past the protrusions (57). The embodiments of the invention describing needle penetration of the distal seal are also applicable with the use of a partial seal or virtual seal formed by protrusions (57) that extend toward or across the lumen at the distal end of the needle.

Generally speaking, and as described above, the device is primed when a deployment force is placed on the cannula such that once the needle reaches the desired site of delivery in the eye (such as the suprachoroidal space or supraciliary space), the cannula is automatically deployed. In this way, the device can be operated with one hand. The only force that needs to be applied by the user is the penetration force to allow the needle to penetrate the distal seal and then the eye tissue. The needle length can be suitably designed to target specific cannulation sites at corresponding depths in the eye. In some embodiments, the device may comprise a retaining means to retain the distal element on the needle once the device is primed.

Prior to deployment of the cannula, the distal element will generally not be in direct physical contact with the elongate body or the barrel. In fact, the distance between the proximal end of the distal element and distal end of the elongate body or barrel (and design of any compressible or collapsible element that may be present) can be arranged to determine the maximum depth of needle penetration. For example, during operation of the device, as the distal seal is pressed against the eye, the distal element and elongate body or barrel will move towards each other. It is this motion that advances the needle tip towards and through the distal seal/tissue interface and into the patient's eye. Once the proximal end of the distal element abuts against the distal end of the elongate body or barrel (or once the compressible or collapsible element does not permit further motion), continued advancement of the needle is prevented. Hence, the distance between the proximal end of the distal element and distal end of the elongate body or barrel may be equal to the maximum depth of needle penetration. Account may need to be taken for any distance between the needle tip and the distal seal/tissue interface and/or the use of any compressible or collapsible element. In particular, the maximum depth of needle penetration and therefore the depth at which the cannula is deployed may be determined by the distance between the proximal end of the distal element and distal end of the elongate body or barrel less the distance between the needle tip and the distal seal/tissue interface. Thus, the position and sizes of the distal element, needle, and distance between the needle tip and distal seal/tissue interface (if any) can be configured to determine a maximum needle penetration depth. The skilled person could design the device accordingly based on the present disclosure.

In this way the device may comprise a means for determining a maximum needle penetration depth to control the cannulation into the eye. The means can be a set distance between the proximal end of the distal element and distal end of the elongate body or barrel (as determined by the relative size of the distal element, the needle, the distance of the needle tip from the distal seal/tissue interface, and the shape and configuration of any compressible or collapsible element present).

Alternatively, the needle may comprise a separate element that halts advancement of the distal element along the needle during operation (such as an element present on the needle disposed between the distal element and the elongate body or barrel, for example an annular ridge or clamp). In some embodiments, this element to prevent further advancement of the distal element along the needle during operation may be moveable such that the maximum needle penetration depth can be determined by the user. In such an embodiment, the needle may comprise markings to allow the user to select an appropriate maximum penetration depth. In another embodiment, the depth of needle penetration may be determined by the compressible element, for example the compressible element only allowing the desired needle advancement by way of increasing rigidity as the element is compressed, or by other mechanical means, such as entrapment of the compressible element between the proximal end of the distal element and distal end of the elongate body or barrel. The present invention therefore provides devices having fixed maximum needle penetration depths suitable for targeting the tissue of interest. Suitable designs to achieve a fixed maximum needle penetration depth would be apparent to the skilled person based on this disclosure. Of course, the maximum depth of needle penetration can be within certain tolerances. Maximum needle penetration depth is also referred to herein as effective needle length.

In one embodiment, the material for administration such as an active agent containing composition is preloaded in the cannulation device, whereby the device serves as the storage container for the material for administration prior to use. In one embodiment, the preloaded device is sterilized for use after placement and sealing of the material for administration in the cannulation device. The sterilization may be accomplished by established methods of sterilization such as heat or ionizing radiation. In one embodiment the material for administration is preloaded in the device as a dry material that is reconstituted with a liquid that is introduced into the device prior to use. The cannulation device may contain a port or connector in fluid communication with the device reservoir to facilitate reconstitution of the material for administration within the cannulation device.

Figure 1B:
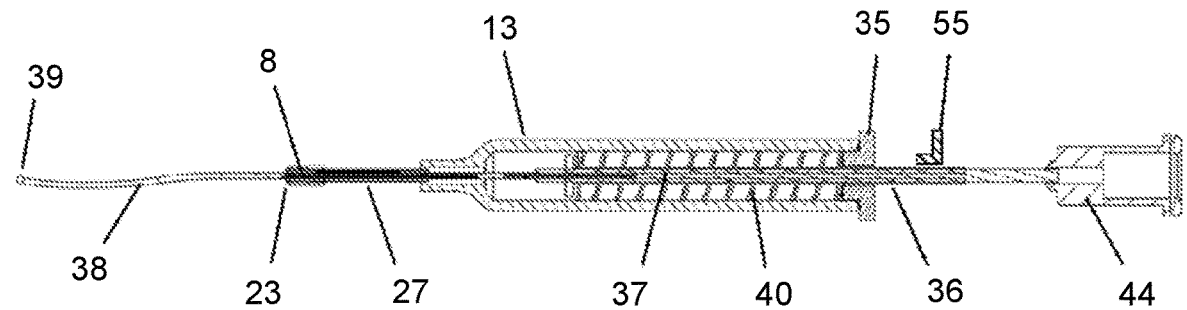
Figure 1C:
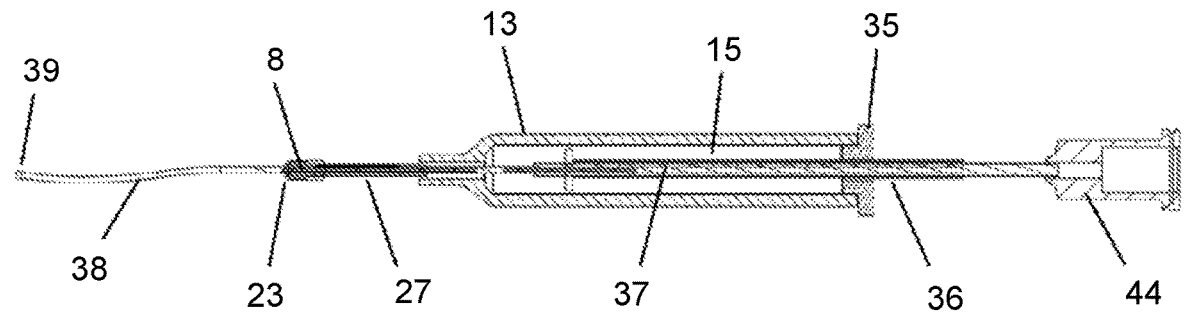
FIG. 1C also depicts another embodiment of a cannulation device for deploying a flexible cannula into a tissue space of an eye.

Embodiments of the cannulation device are depicted in FIG. 1A and FIG. 1B. The device comprises a hollow barrel 13, with a proximal barrel end cap 35. A plunger 36 slidably passes through the end cap. The plunger has a lumen 37, through which passes a flexible cannula tubular element 38. The flexible cannula 38 is fixed in place to the plunger 36. This distal tip of the flexible cannula has a rounded atraumatic tip 39. A plunger compression spring 40, provides a distally directed force on the plunger 36 and flexible cannula 38. A beveled needle 8 is attached and fixed to the distal end of the barrel 13 such that the needle 8 does not move in relation to the barrel 13 to provide direct control of the location of the needle tip when manipulating the position of the barrel 13. The flexible cannula 38 moves distally under the force of the plunger compression spring 40 when the tissue interface and distal seal 23 is opened by the distal tip of the needle 8. The tissue interface and distal seal 23 is attached to the distal end of a collapsible element 27. The collapsible element 27 is attached to the distal end of the barrel 13 and provides a distally directed force on the tissue interface and distal seal 23 thereby pressing the tissue interface and distal seal 23 onto the tissue surface. The proximal end of the flexible cannula 38 terminates in an interface such as a Luer fitting 44 to allow delivery of a material for administration through the flexible cannula 38.

Figure 2:
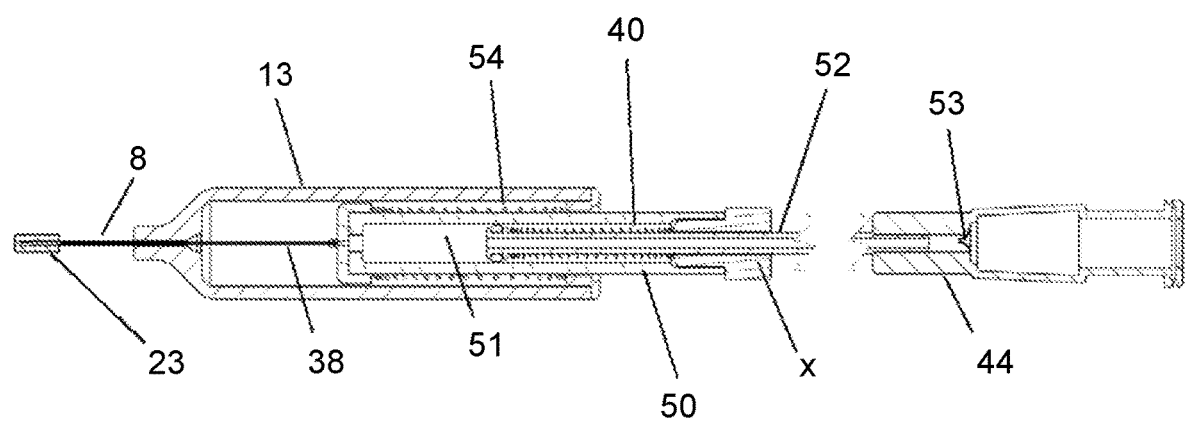
FIG. 2 depicts one embodiment of a cannulation device for deploying a flexible cannula into a tissue space of an eye, with a reservoir to contain a material for administration.

One embodiment of the cannulation device is depicted in FIG. 2. The device is configured as a hollow barrel 13, with a hollow body 50 residing slidably within the hollow barrel and containing a reservoir 51 for the material to be administered. The distal end of the reservoir body 50 is connected to a flexible cannula tubular element 38. A tubular reservoir plunger 52 resides slidably inside the reservoir and a connector such as a Luer fitting 44 is attached at the proximal end of the reservoir plunger to allow filling of the reservoir. The connector incorporates a one way valve 53 to prevent reflux of the material to be administered after filling of the reservoir. A reservoir plunger compression spring 40 provides the force to expel the material to be administered.

The reservoir body 50 acts as a plunger within the hollow barrel for the deployment of the flexible tubular cannula 38. A reservoir compression spring 54 resides over the reservoir body 50. The reservoir compression spring 54 provides the force to deploy the flexible cannula 38.

A beveled needle 8, is attached and fixed to the distal end of the barrel 13, such that the needle 8 does not move in relation to the barrel 13 to provide direct control of the location of the needle tip when manipulating the position of the barrel 13. The flexible cannula 38 moves distally under the force of the reservoir compression spring 40 when the tissue interface and distal seal 23 is opened by the distal tip of the needle 8.

Figure 3:
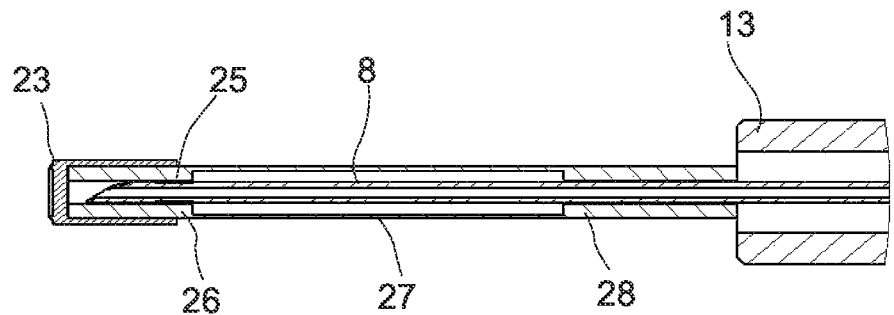
FIG. 3 depicts one embodiment of a distal tip of a cannulation device with a collapsible element.
Figure 4A:
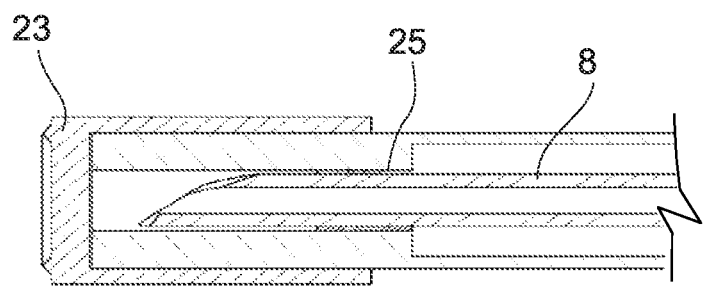
FIG.4A depicts magnified detail of one embodiment of a distal tip of a cannulation device with a collapsible element and FIG. 4B depicts magnified detail of another embodiment of a distal tip of a cannulation device with a collapsible element.
Figure 4B:
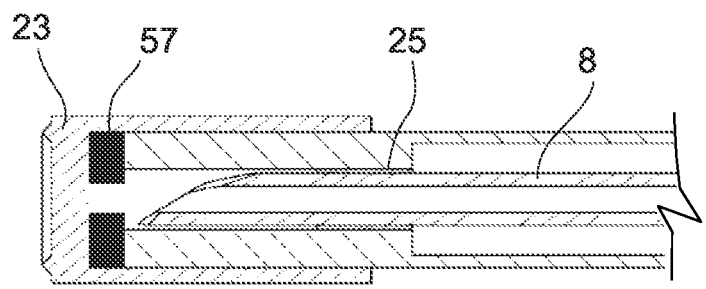
Figure 5:
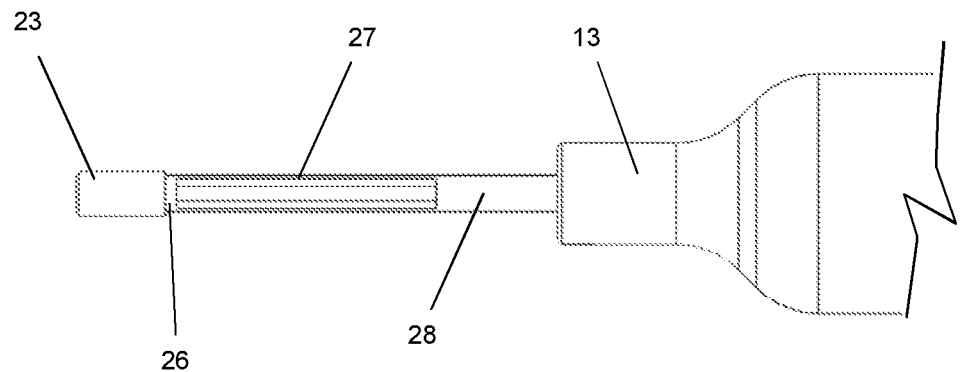
FIG. 5 depicts one embodiment of a distal tip of a cannulation device in an uncollapsed state.
Figure 6:
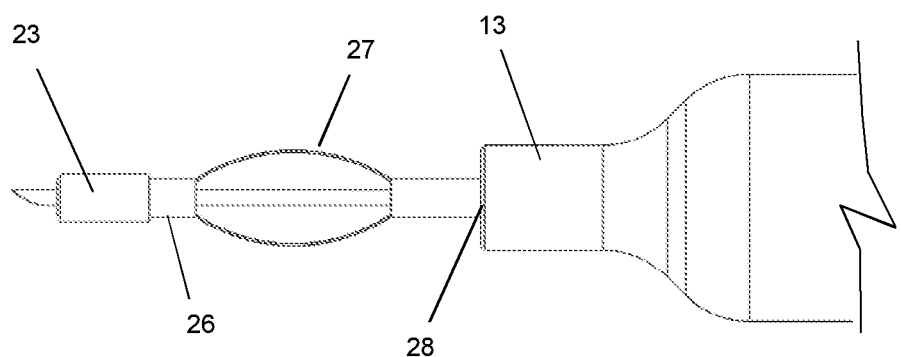
FIG. 6 depicts one embodiment of a cannulation device in a collapsed state.

In one embodiment, the distal tip of the device is comprised of collapsible elements. Referring to the device depicted in FIG. 3 and the magnified device distal tip detail in FIG. 4A, the distal tip is comprised of a distal segment, a central collapsible segment and a proximal segment. The tissue interface and distal seal 23 is disposed about a distal tubular shaft 26. The inner lumen of the distal tubular shaft 26 contains an internal seal 25 which seals the space between the tubular distal shaft 25 and the beveled needle 8. The central segment is comprised one or more segments 27 which function as collapsible elements. The collapsible elements 27 are attached or integral to the distal tubular shaft 26 and proximal tubular shaft 28. The proximal tubular shaft 28 is connected to the barrel 13 of the device providing an anchor point for the collapsible element and preventing distal movement of the tissue interface and distal seal 23. FIG. 5 shows the distal segment of the device in an uncollapsed state. The tissue interface and distal seal 23 and the distal tubular shaft 26 are disposed at the end of the collapsible elements 27. The proximal tubular shaft 28 is anchored to the barrel 13. FIG. 6 shows the distal segment of the device in a collapsed state. The force of advancing the device into the tissue causes the collapsible elements 27 to deform, allowing the distal tubular shaft 26 and tissue interface and distal seal 23 to slide proximally along the needle 8 toward the distal end of the barrel 13. The distal tip of the needle 8 has penetrated the tissue interface and distal seal 23.

Figure 7:
FIG. 7 depicts one embodiment of a cannulation device needle with a curved distal tip to direct the cannula at an angle from the long axis of the needle.
Figure 8:
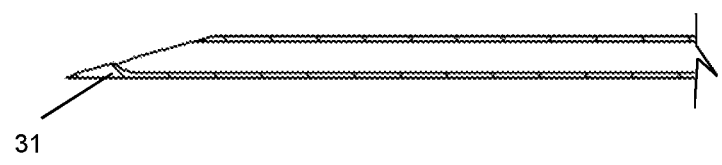
FIG. 8 depicts one embodiment of a cannulation device needle with an inner deflecting element in the needle lumen at the distal tip to direct the cannula at an angle from the long axis of the needle.
Figure 9:
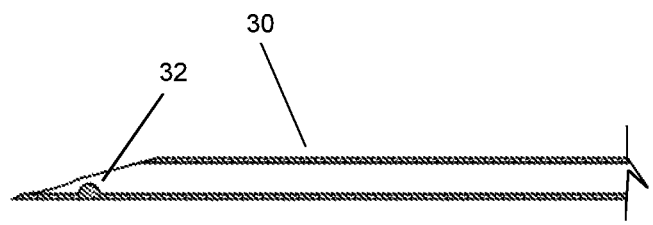
FIG. 9 depicts one embodiment of a cannulation device needle with a localized inner deflecting element in the needle lumen at the distal tip to direct the cannula at an angle from the long axis of the needle.

In some embodiments, the distal tip of the needle is configured to direct the tubular element at an angle from the long axis of the needle. Referring to the needle tip depicted in FIG. 7, the distal tip of the needle 29 may be curved to direct the tubular element. Referring to the needle tip depicted in FIG. 8, the distal tip of the needle 30 may have an inner deflecting element 31 in the lumen of the needle in the region of the bevel of the needle. Referring to the needle tip depicted in FIG. 9, the distal tip of the needle 30 may have a localized inner deflecting element 32 in the lumen of the needle in the region of the bevel of the needle.

The described embodiments of the cannulation device may be used in combination to cannulate a tissue space and administer a fluid, semisolid or solid. The configuration of the distal portion of the cannulation device comprises the distal element which functions as a tissue interface and distal seal on the distal end of the needle. The cannula and reservoir for the delivery material may be configured for administration of a fluid, semisolid, solid or implant from the cannula. In some embodiments, the lumen of the cannula may also act as the reservoir or a portion of the reservoir of the material for administration.

For use in the cannulation device, a lubricant or lubricious coating may be used to aid cannulation. The lubricant may be used to coat the cannula or the needle lumen. The lubricant may also be placed in the lumen of the distal element to coat the tip of the cannula and the outer surface of the needle as it passes into tissue. The distal end of the needle lumen may also act as a small reservoir for the lubricant to coat the cannula during deployment. Suitable lubricants include, but are not limited to, oils, waxes, lipids, fatty acids, polymers and polymer solvent mixtures. Polymers include, but are not limited to, water soluble polymers such as polyethylene glycol and polypropylene glycol, and polymer lubricants such as polysiloxane. Polymer solvent mixtures include, but are not limited to, aqueous formulations of water soluble polymers such as polyethylene oxide, polyvinylpyrrolidone and glycosaminoglycans.

The material for administration may be a fluid, semisolid or solid composition of an active agent for delivery into the suprachoroidal space, supraciliary space or other spaces of the eye such as the vitreous cavity, subconjunctival space, sub-Tenon's space and sub-retinal space. The active agent may be solubilized or dispersed in a fluid, semisolid or solid composition. The active agent may also be distributed in the composition as particles. In one embodiment, the composition comprises a plurality of drug-containing particles 45 formed into a semisolid 46, shown schematically in FIG. 10. For delivery of the semisolid in the suprachoroidal space or supraciliary space, the composition is placed into the eye from the outer surface of the eye through the cannula to preferentially locate the material in the suprachoroidal space or supraciliary space near the distal end of the cannula. After placement in the suprachoroidal space or the supraciliary space, the semisolid composition transforms, degrades or dissolves into individual drug-containing particles that may migrate in the space to distribute the active agent. The semisolid mass of drug particles allows a large amount of drug to be injected in a very small volume to prevent an acute increase of intraocular pressure such as occurs with administration of an equivalent amount of drug suspended in a fluid. The semisolid formulation enables an effective amount of drug to be delivered in the range of 5 to 50 microliters, 10 to 40 microliters or 15 to 35 microliters.

In one embodiment, the composition comprises a plurality of drug-containing particles 47 formed into a formed solid 48, shown schematically in FIG. 11A and FIG. 11B. The formed solid 48 comprising the plurality of drug-containing particles 47 may be in the shape of a plug, tube or cylinder. In one embodiment, the formed solid is an elongated body with a diameter approximately the inside diameter of the cannula used for placement of the formed solid in the tissue space. The diameter may range from 0.60 mm to 0.159 mm. Depending on the dose of active agent and active agent content of the particles, the formed solid may have a length ranging from 1 mm to 50 mm (for example 1 mm to 25 mm). After placement in the suprachoroidal space or the supraciliary space, the formed solid composition transforms, degrades or dissolves into individual active agent containing particles that may migrate in the space. The formed solid mass of particles allows a large amount of active agent to be injected in a very small volume to prevent an acute increase of intraocular pressure such as occurs with administration of an equivalent amount of active agent suspended in a fluid. The volume of the injected formed solid may range from 0.1 microliters to 10 microliters (for example 0.1 to 5 microliters).

The particles of active agent may be in the form of a selected size range of crystals of the active agent. The particles of active agent may be in the form of microspheres by fabrication of the active agent into the form of spherical particles or by the formulation of the active agent with a polymer and fabricating microspheres from the combination. Microspheres containing active agent may be fabricated by any of the known means for microsphere fabrication such as by spray drying, emulsion or coacervation. The use of a non-toxic polymer to hold active agent within microspheres allows tailoring of the active agent release rate by the polymer composition, active agent content and size of the microspheres. Microspheres with an active agent content of 10-90 weight % may provide appropriate release. The use of polymers of selected solubility allows both water soluble and water insoluble active agents to be incorporated into microspheres. Suitable polymers include, but are not limited to, non-toxic water soluble polymers such as polyvinylpyrrolidone, polyvinylpyrrolidone co-vinyl acetate, polyvinyl alcohol, polyethylene glycol and polyethylene oxide, biodegradable polymers such as polyhydroxybutyrate, polydioxanone, polyorthoester, polycaprolactone, polycaprolactone copolymers, poly lactic acid, poly glycolic acid, poly lactic-glycolic acid copolymers and poly lactic-glycolic acid-ethylene oxide copolymers, and biological polymers such as gelatin, collagen, glycosaminoglycans, cellulose, chemically modified cellulose, dextran, alginate, chitin and chemically modified chitin.

Alternatively, active agent particles of approximately spherical shape or other uniform shapes may be prepared by milling of larger active agent particles or by controlled crystallization. Active agent particles and active agent containing microspheres may also be individually coated with a polymer layer to form active agent particles with an external surface coating or barrier coating. The coatings may comprise non-toxic water soluble polymers including, but not limited to, polyvinylpyrrolidone, polyvinylpyrrolidone co-vinyl acetate, polyvinyl alcohol, polyethylene glycol and polyethylene oxide, biodegradable polymers such as polyhydroxybutyrate, polydioxanone, polyorthoester, polylactic acid, polyglycolic acid, poly lactic-glycolic acid copolymers, acid terminated polylactic-glycolic acid copolymers, polylactic-glycolic acid-ethylene oxide copolymers, polylactic acid-polyethylene glycol copolymers, polycaprolactone, polycaprolactone copolymers and polycaprolactone-polyethylene glycol copolymers, and biological materials such as gelatin, collagen, glycosaminoglycans, cellulose, chemically modified cellulose, dextran, alginate, chitin, chemically modified chitin, lipids, fatty acids and sterols.

In one embodiment, the plurality of active agent containing particles is formed into a solid or semisolid with an excipient. Suitable excipients include, but are not limited to, non-toxic water soluble polymers such as polyvinylpyrrolidone, polyvinylpyrrolidone co-vinyl acetate, polyvinyl alcohol, polyethylene glycol and polyethylene oxide, biodegradable polymers such as polyhydroxybutyrate, polydioxanone, polyorthoester, polycaprolactone, polycaprolactone copolymers, polylactic acid, polyglycolic acid, polylactic-glycolic acid copolymers and polylactic-glycolic acid-ethylene oxide copolymers, and biological materials such as gelatin, collagen, glycosaminoglycans, cellulose, chemically modified cellulose, dextran, alginate, chitin and chemically modified chitin. The solid or semisolid composition may be formulated with a mixture of different excipients. The active agent containing particles are mixed with the excipient in a suitable solvent that dissolves or forms a dispersion of the excipient, but does not extract the drug from the particles or dissolve the particles. In one embodiment, a semisolid composition is injected as a mixture, dispersion or suspension with a solvent. In one embodiment, the solid or semisolid composition is formed in a mold or extruded and allowed to dry to form a solid of desired dimensions for administration. Ideal for administration of the formed solid or semisolid composition is an elongated shape with an outer diameter sized to fit within the lumen of a small diameter cannula, 20 gauge or smaller, corresponding to 0.60 mm diameter or smaller. In one embodiment, the formed solid or semisolid composition has an outer diameter sized to fit within the lumen of a 25 gauge or smaller cannula, corresponding to a 0.26 mm diameter or smaller.

In one embodiment, the semisolid composition is dried, such as by lyophilization or air drying, for rehydration prior to administration. The semisolid composition may have excipients to aid reconstitution such as salts, sugars, water soluble polymers and surfactants. In one embodiment, the active agent containing particles are sized smaller than the inner diameter of the cannula to allow close packing of the particles within a formed solid or semisolid to enhance mechanical properties. Such active agent containing particles would have an average diameter in the range of 5 to 100 microns, for example 10 to 50 microns, and may comprise a mixture of diameters to facilitate close packing. The mean or median diameter of the particles may be in the range of 5 to 100 microns, for example 10 to 50 microns, 10 to 40 microns, 10 to 30 microns or 10 to 20 microns.

The dispersion and migration of the active agent containing particles are desired to promote a uniform distribution of the particles in the eye. The dissolution of the excipient and resultant release of active agent containing particles may be triggered by the absorption of fluid from the tissue space, for example due to the ionic environment or the temperature of the environment. In one embodiment, the excipient comprises a lipid or fatty acid with a melting temperature between room temperature and the temperature of the ocular tissues space, approximately 37 degrees centigrade (for example, a melting temperature between 21 and 37 degrees centigrade, between 25 and 37 degrees centigrade, or between 30 to 35 degrees centigrade). The rate of release of the individual active agent containing particles from the solid or semisolid composition may be tailored by the addition of hydrophilic or amphiphilic agents that increase the dissolution rate of the excipients of the solid or semisolid composition. The release of the active agent containing particles may occur over hours, days or weeks, depending on the amount and composition of the material for administration. For example, a maximum (or minimum, depending on the formulation) of 50% of the active agent containing particles may be released after 1 hour, 6 hours, 12 hours, 1 day, 3 days or 1 week.

The solid or semisolid composition may act by the ionic environment of the tissue space to provide dissolution, as may be provided by ionically crosslinked polymers such as sodium alginate. The solid or semisolid composition may be triggered for dissolution in the tissue space by temperature, such as with lipids and fatty acids with a melt transition temperature greater than room temperature, approximately 20 degrees centigrade, and less than or equal to the temperature within the ocular tissue space, approximately 37 degrees centigrade. Such lipids and fatty acids include, but are not limited to, capric acid, erucic acid, 1,2-dinervonoyl-sn-glycero-3-phosphocholine, 1,2-dimyristoyl-sn-glycero-3-phosphocholine, and 1,2-dipentadecanoyl-sn-glycero-3-phosphocholine and mixtures thereof.

Due to the small size of the active agent containing particles, active agent release from the particles may be too rapid to provide sustained active agent effect after administration to the eye. It is an object of the invention to provide active agent containing particles with prolonged release kinetics (i.e. controlled release formulations). In one embodiment the active agent is incorporated into a polymer matrix that creates a poor diffusion path for the drug thereby slowing active agent release as compared to the active agent without a polymer matrix. In one embodiment, the active agent containing particle is coated with a barrier such as a polymer or other compound. The barrier material typically has different chemical properties than the active agent so that the active agent is not readily soluble through the barrier coating and is slowed in active agent release as compared to the active agent containing particle without a barrier coating. One method for selection of the barrier coating is a material with a different partition coefficient or log P than the active agent, with an increased difference providing an increased barrier to active agent release. In one embodiment, the individual particles of an active agent, are coated with a barrier coating of increased water solubility or decreased log P compared to the active agent to form a barrier coating on each particle. Barrier materials may include, but are not limited to, acid terminated poly lactic-glycolic acid copolymers, polylactic acid-polyethylene glycol copolymers and polycaprolactone-polyethylene glycol copolymers. In one embodiment, the individual particles of an active agent are coated with a barrier coating of decreased water solubility or increased log P compared to the active agent to form a barrier coating on each particle including, but not limited to, a hydrophobic polymer, lipid, fatty acid or sterol. Active agent particles may be coated by any of the known means for particle coating, for example, spray drying, electrostatic spraying or chemical deposition. In one embodiment, shown schematically in FIG. 11A and FIG. 11B, the formed solid or semisolid material 48 comprises a plurality of active agent particles 47 encapsulated or coated with a barrier material 49, such as a soluble polymer or other coating, to modify the active agent release characteristics and/or the mechanical properties.

While the active agent of the composition is primarily contained in the plurality of particles, some active agent may also be formulated into the excipient. The active agent in the excipient may act to prevent extraction or diffusion of active agent from the particles during processing or storage. The active agent in the excipient may also act to provide a rapid release component to the active agent formulation to initiate therapeutic effect of the active agent while allowing the active agent in the particles to provide a sustained delivery to maintain the treatment effect.

In one embodiment, the active agent composition comprises an active agent and an excipient comprising a biodegradable or bioerodible material. The biodegradable or bioerodible material may be comprised of, for example but not limited to, polyhydroxybutyrate, polydioxanone, polyorthoester, polycaprolactone, polycaprolactone copolymer, polycaprolactone-polyethylene glycol copolymer, polylactic acid, polyglycolic acid, polylactic-glycolic acid copolymer, acid terminated polylactic-glycolic acid copolymer, or polylactic-glycolic acid-ethylene oxide copolymer, gelatin, collagen, glycosaminoglycan, cellulose, chemically modified cellulose, dextran, alginate, chitin, chemically modified chitin, lipid, fatty acid or sterol. The active agent may be dispersed in the biodegradable or bioerodible material as an amorphous solid dispersion. The active agent may be dispersed in the biodegradable or bioerodible material as a plurality of active agent crystals. The active agent may be dispersed in the biodegradable or bioerodible material as both an amorphous solid dispersion and as active agent crystals. The active agent composition is shaped as an elongate solid body or a semisolid for administration into the ocular tissue space. Release of the active agent from the composition allows the active agent to diffuse into the tissues of the eye and may be assisted by the flow of fluid in the tissue space. In the case where the active agent is in the form of a solid amorphous dispersion, the biodegradable or bioerodible material is selected to provide the desired active agent loading and release characteristics of the active agent In the case where the active agent is in the form of dispersed crystals, the amount of active agent, the biodegradable or bioerodible material characteristics and the crystal form of the active agent may be selected to provide the desired active agent loading and release characteristics of the active agent. The active agent crystals may also be coated with an excipient to reduce the active agent release rate of the active agent composition. In one embodiment, the composition has an extended release of the active agent. The active agent elution from the composition may have a half-life in the range of 14 to 180 days, 21 to 90 days or 30 to 60 days.

A variety of drugs as active agents may be delivered by the present invention to the eye for the treatment of ocular diseases and conditions including inflammation, infection, macular degeneration, retinal degeneration, neovascularization, proliferative vitreoretinopathy, glaucoma and edema. Useful drugs include, but are not limited to, steroids, non-steroidal anti-inflammatory agents, antibiotics, VEGF inhibitors, PDGF inhibitors, anti-TNF alpha agents, mTOR inhibitors, cell therapies, neuroprotective agents, anti-hypertensive agents, antihistamines, aminosterols and nucleic acid based therapeutics. The drugs may be in the form of soluble solutions, suspensions, gels, semisolids, microspheres, formed solids or implants.

In one embodiment, the active agent is preloaded in the device prior to use during the time of manufacture. The source of force to provide a deployment force to the cannula may be activated just prior to or simultaneous with use. In one embodiment the activation is achieved by a mechanism (55) to preload the force element, such as compressing a spring, from the exterior of the device such as by a movable proximal handle attached to the plunger. In one embodiment, the source of force is preloaded during manufacture and the preloaded force is stabilized by means of a stop mechanism. Prior to or simultaneous with use, the stop mechanism is released, thereby placing the deployment force on the cannula prior to contact or penetration of the eye and the cannula deployment is triggered by the advancement of the needle into the eye as with previous embodiments of the invention.

As noted, a variety of drugs as active agents may be delivered by the present invention to the eye for the treatment of a variety of ocular diseases and conditions including inflammation, infection, macular degeneration, retinal degeneration, neovascularization, proliferative vitreoretinopathy, glaucoma, and edema. Useful drugs include, but are not limited to, steroids such as corticosteroids including dexamethasone, fluocinolone, loteprednol, difluprednate, fluorometholone, prednisolone, medrysone, triamcinolone, betamethasone and rimexolone; non-steroidal anti-inflammatory agents such as salicylic-, indole acetic-, aryl acetic-, aryl propionic- and enolic acid derivatives including bromfenac, diclofenac, flurbiprofen, ketorolac tromethamine and nepafenac; antibiotics including azithromycin, bacitracin, besifloxacin, ciprofloxacin, erythromycin, gatifloxacin, gentamicin, levofloxacin, moxifloxacin, ofloxacin, sulfacetamide and tobramycin; VEGF inhibitors such as tyrosine kinase inhibitors, antibodies to VEGF, antibody fragments to VEGF, VEGF binding fusion proteins; PDGF inhibitors, antibodies to PDGF, antibody fragments to PDGF, PDGF binding fusion proteins; anti-TNF alpha agents such as antibodies to TNF-alpha, antibody fragments to TNF-alpha and TNF binding fusion proteins including infliximab, etanercept, adalimumab, certolizumab and golimumab; mTOR inhibitors such as sirolimus, sirolimus analogues, Everolimus, Temsirolimus and mTOR kinase inhibitors; cell therapies such as mesenchymal cells or cells transfected to produce a therapeutic compound; neuroprotective agents such as antioxidants, calcineurin inhibitors, NOS inhibitors, sigma-1 modulators, AMPA antagonists, calcium channel blockers and histone-deacetylases inhibitors; antihypertensive agents such as prostaglandin analogs, beta blockers, alpha agonists, and carbonic anhydrase inhibitors; aminosterols such as squalamine; antihistamines such as H1-receptor antagonists and histamine H2-receptor antagonists; and nucleic acid based therapeutics such as gene vectors, plasmids, guide RNA and siRNA.

In one embodiment of the invention, there is provided the drug composition of the invention for use in medicine, in particular for use in ocular medicine. In a further embodiment of the invention, there is provided the drug composition of the invention for use in the treatment of an ocular disease or condition. The ocular disease or condition may be inflammation, infection, macular degeneration, retinal degeneration, neovascularization, proliferative vitreoretinopathy, glaucoma or edema. In some embodiments, the drug composition is administered by delivery through a cannula, in particular a cannula placed by the cannulation device of the present invention.

One aspect includes the use of a drug composition in the treatment of an ocular disease or condition. Such uses therefore also include the use of a drug composition in the manufacture of a medicament for treating an ocular disease or condition.

In one embodiment there is provided a method of treating an ocular disease or condition by administration of a drug composition by a cannulation device of the present invention to the eye, for example to the suprachoroidal space or to the supraciliary space. The drug composition may dissolve or transform into a plurality of drug-containing particles that migrate from the site of administration (for example the suprachoroidal space or supraciliary space) after administration. The ocular disease or condition may be inflammation, infection, macular degeneration, retinal degeneration, neovascularization, proliferative vitreoretinopathy, glaucoma or edema.

In another embodiment of the invention there is provided a kit of parts comprising the cannulation device described herein and the drug composition of the invention. The drug composition may be provided preloaded into the delivery device. Alternatively, the drug composition may be provided as a plurality of discrete dosage forms suitable for insertion into the delivery device. Therefore a kit may also provide the drug composition of the invention in the form of a plurality of discrete dosage forms along with the cannulation device.

Preferred features of the second and subsequent embodiments of the invention are as for the first embodiment mutatis mutandis.

The invention will now be described in reference to a number of examples, which are provided for illustrative purposes and are not to be construed as limiting on the scope of the invention.

EXAMPLES

Example 1

Cannulation Device for Placement of a Flexible Cannula in the Suprachoroidal Space A device according to an embodiment of the invention was fabricated to deploy a flexible cannula into the suprachoroidal or supraciliary space of the eye. A barrel element was fabricated by cutting off the proximal end of a 0.5 ml insulin syringe to a barrel length of 30 mm. The integral needle was removed from the barrel to allow the attachment of standard Luer hub needles. The distal tip of the barrel was cut off leaving a remaining section of Luer taper capable of securely holding a Luer hub needle. A barrel end cap was fabricated from a nylon 10-32 socket head cap screw with a thread length of 4.5 mm. A through hole of 1.86 mm diameter was drilled through the end cap to allow the plunger to freely slide through the end cap. A plunger shaft was fabricated from a tubular Teflon coated stainless steel rod with an outer diameter of 1.8 mm and an inner diameter of 0.8 mm and a length of 43 mm. The distal end of the shaft was turned down to a diameter of 1.74 mm and a stainless steel washer of 4.1 mm outer diameter, 1.70 mm inner diameter and 0.5 mm thickness was press-fit onto the rod to provide a distal stop for the plunger spring. The proximal end of the rod was drilled out to 1.55 mm diameter. A compression spring with an outer diameter of 3.1 mm and a wire diameter of 0.18 mm and a length of 31.8 mm was placed over the shaft of the plunger and the barrel end cap was then slid over the plunger shaft proximal to the spring. The plunger assembly was placed into the barrel housing and the end cap was press fit into the barrel proximal end, securing the plunger assembly within the barrel.

A deflecting needle was fabricated from a 27 gauge×13 mm thin walled hypodermic needle. The distal tip of the needle was bent towards the bevel to create a ramp-like inner surface. The back side of the needle, opposite of the original bevel, was ground in a manner similar to a standard needle lancet tip with primary and secondary bevels to yield a sharp tip for tissue penetration. A 24 gauge thin walled tube 3 cm long was press fit into the needle hub butting up against the proximal end of the 27 gauge needle. The 24 gauge tube acted as a support tube to prevent the flexible cannula from kinking during deployment. The needle assembly was mounted onto the barrel assembly.

A flexible cannula was fabricated. The cannula shaft was comprised of a proximal segment of PEBAX polymer tubing of Shore 72D durometer 50 mm long with an inner diameter of 0.30 mm and an outer diameter of 0.38 mm. The proximal end of the proximal segment was attached to a 30 gauge blunt Luer tubing adapter. A distal segment of polyolefin polymer tubing 75 mm long with an inner diameter of 0.12 mm and an outer diameter of 0.20 mm was adhesively bonded to the distal end of the proximal segment. A nickel-titanium (Nitinol) stiffening wire 0.75 mm diameter was inserted into the flexible cannula to provide pushability for the thin walled distal cannula tube. The distal end of the cannula was formed into a rounded, atraumatic tip using cyanoacrylic adhesive. The flexible cannula was inserted through the plunger and needle assembly and then fixed in place at the proximal end of the plunger shaft. When fully deployed, the flexible cannula extended 15 mm beyond the tip of the needle.

A safety mechanism was incorporated into the device to prevent premature activation of the plunger by the plunger spring force. Two shallow grooves 180 degrees apart and perpendicular to the axis of the plunger were made in the plunger at a distance of 19 mm from the distal tip. The distance between the groove faces was 1.5 mm. A securement clip was fabricated from brass sheet with a width of 6.3 mm and a length of 18 mm. A slot with a width of 1.6 mm and a length of 8.8 mm was machined into the securement clip. The slot was cut in the center of the short side of the securement clip and traversing in the long axis direction.

A molded cylindrical tissue interface and distal seal element was fabricated from 70 Shore A durometer silicone rubber. The distal element had a length of 3.7 mm and a diameter of 1.75 mm. The distal element had a lumen of 2.7 mm length and 0.38 mm diameter. The distal end of the lumen of the distal element was configured with a beveled shape which conformed to the distal end of needle. The distal seal element was attached to the distal tip of the needle such that the needle bevel was in contact with the lumen bevel in order to seal the distal tip of the needle. The non-beveled section of the lumen acted as a slidable seal on the shaft of the needle and provided enough frictional force against the needle shaft to maintain the distal tip against the eye surface during advancement of the needle through the distal seal of 1 mm thickness.

For use, the plunger was retracted thereby compressing the plunger spring and withdrawing the flexible cannula until the plunger grooves were exposed proximally to the end cap. The securement clip was placed over the plunger such that the slot on the securement clip engaged the grooves on the plunger shaft. The securement clip then was held against the proximal end surface of the end cap by the spring force, preventing movement of the plunger.

A 1 cc syringe was filled with 0.5 ml of 0.01% fluorescein solution. The syringe was attached to the female Luer fitting on the proximal end of the cannula. A cadaver porcine eye was prepared by inflating the posterior chamber to a pressure of approximately 20 mm Hg. A target penetration location 4 mm posterior of the limbus of the eye was chosen for insertion of the device needle for deployment of the flexible cannula. The securement clip was removed from the plunger shaft. The tissue interface and distal seal was placed against the scleral surface and the needle tip was then advanced through the distal seal and into the tissues with the needle bevel oriented towards the posterior of the eye. Once the needle lumen reached the suprachoroidal space, the cannula was free to exit the needle and was deployed by the push rod under the plunger spring force. Once the plunger was seen to have been activated, 0.05 ml of fluorescein was injected through the flexible cannula and into the suprachoroidal space. A radial incision was made over the location of the flexible cannula, through the sclera to expose the suprachoroidal space. Once the space was entered, fluorescein solution was seen escaping from the space and further cut-down allowed for direct visualization of the flexible cannula shaft in the suprachoroidal space.

Example 2

Cannulation Device for Placement of a Flexible Cannula in the Suprachoroidal Space A device according to an embodiment of the invention was fabricated. The device comprised a cannula element, a needle with a distal seal, a cannula support element, a force element and a housing body.

The cannula element was fabricated to consist of a distal flexible tubular segment, a connection tube and a proximal Luer adapter to complete the flow path for the material to be administered. The distal flexible tubular element was fabricated from 72D durometer PEBAX tubing 75 mm long with an inner diameter of 0.12 mm and an outer diameter of 0.18 mm. The proximal end of the flexible cannula was pulled through a polyimide support tube 25 mm long with an inner diameter of 0.18 mm and an outer diameter of 1.59 mm, such that 20 mm of the flexible cannula extended proximally from the support tube. A support spring was fabricated from nickel titanium alloy (Nitinol) wire of 0.1 mm diameter. The support spring was 25 mm long with an inner diameter of 0.2 mm. The spring was wound with a pitch of 0.48 mm and had closed ends. The Nitinol spring was shape set by application of hot air at 480° C. The support spring was placed over the polyimide support tube. The support tube and spring prevented the collapse or kinking of the flexible cannula inside the cannula support element. The proximal end of the flexible cannula was bonded inside a polyetheretherketone (PEEK) tube 10 mm long with an inner diameter of 0.17 mm and an outer diameter of 1.59 mm, with 10 mm of the flexible tube extending proximally from the PEEK tube. A connection tube comprised of polyethylene 250 mm long with an inner diameter of 0.28 mm and an outer diameter of 0.61 mm was placed over the exposed distal end of the flexible cannula and bonded to the PEEK tube.

The needle was fabricated from a 27 gauge thin walled needle 32 mm long. The needle was adhesively bonded into a polyethylene Luer hub with the beveled tip of the needle extending 3 mm from the distal end of the hub. The distal seal was fabricated from molded 50A durometer silicone elastomer with a length of 3 mm and an outer diameter of 0.75 mm. The proximal end was configured with a blind hole 2.1 mm long and 0.3 mm diameter and with a flat distal end. The distal seal was placed on the needle at the final step of the device assembly.

The cannula support element was fabricated from a distal tube, a connector tube and a proximal tube. The distal tube was fabricated from PEEK tubing 30 mm long with an inner diameter of 0.5 mm and an outer diameter of 1.59 mm. The proximal support element tube was fabricated from stainless steel tubing 110 mm long with an inner diameter of 1.32 mm and an outer diameter of 1.57 mm. A support element connector tube was fabricated from acetal (Delrin) tubing 25 mm long with an inner diameter of 1.59 and an outer diameter of 3.2 mm. The proximal end of the support element connector tube was bored to a diameter of 1.9 mm to accept the distal end of a force element spring support tube. The distal support element tube was placed over the flexible cannula and butted up to the cannula PEEK tube, covering the segment containing the support tube and support spring. The proximal support tube was placed over the cannula connection tube and adhesively bonded to the cannula PEEK tube. The support element connector tube was placed over the distal tube, cannula PEEK tube and proximal support tube junctions thereby holding the assembly together.

The force element was fabricated from a spring support tube, a compression spring and a proximal adjustable stop. The force element spring support tube was fabricated from stainless steel tubing 140 mm long with an inner diameter of 1.6 mm and an outer diameter of 2 mm. The compression spring was fabricated from stainless steel spring temper wire with a diameter of 0.26 mm. The compression spring was 100 mm long with an inner diameter of 2.6 mm and a pitch of 1.4 mm with closed ends. The adjustable stop was fabricated from a 10-32 nylon socket head cap screw 38 mm long with a hole of 2.2 mm diameter drilled through the axis. The spring support tube was placed over the polyethylene cannula connection tube and press fit into the proximal end of the Delrin cannula support element connector tube, thereby completing a subassembly consisting of the cannula element, cannula support element and spring support tube.

The housing body was constructed from a distal and proximal body fabricated from modified polycarbonate 1 mm syringe bodies. The distal body was modified by cutting off the finger flanges, then drilling and tapping the proximal end with a ⁵⁄₁₆-18 thread, 8 mm deep. The syringe distal Luer lock connector was retained. The proximal body was modified by cutting off the finger flanges, then drilling and tapping the proximal end with a 10-32 thread, 19 mm deep. The distal end of the proximal body was machined down and threaded to a ⁵⁄₁₆-18 thread that was 7.6 mm in length. In this manner, the distal and proximal bodies were attached via the ⁵⁄₁₆-18 threaded portions for assembly of the device.

The device was assembled by placing the cannula element, cannula support element and force element spring support tube subassembly into the distal housing. The compression spring was placed over the spring support tube and the proximal housing was attached to the distal housing. The distal end of the flexible cannula was inserted into the lumen of the needle and the needle and needle Luer hub was attached to the distal housing Luer connector. The proximal end of the needle was slidably disposed within the distal PEEK tube of the cannula support element. The proximal end of the needle abutted the cannula support spring. The force element adjustable stop was placed over the cannula connector tube and threaded into the proximal end of the proximal housing. A 30 gauge Luer needle adapter was inserted into the proximal end of the cannula connector tube to allow connection of a syringe for delivery of the material to be administered.

With the mechanism in the deployed configuration, the flexible cannula was configured to extended 12 mm from the distal tip of the needle. The adjustable stop was screwed into the assembly so that the force element compression spring had just enough force to overcome the compression of the cannula support spring, allowing deployment of the cannula when the device was activated. The proximal end of the force element support rod protruded from the proximal end of the adjustable stop. A silicone O-ring with a tight fit on the force element support rod was temporarily placed over the support rod. The O-ring was used to hold the mechanism in the retracted configuration while the distal seal was placed over the needle tip. The O-ring was removed which set the device in a state ready for deployment.

A 0.25 ml syringe was filled with 100 microliters of 0.1% fluorescein solution and was attached to the proximal Luer fitting of the device. A cadaver porcine eye was prepared by inflating it to a pressure of 17 mm Hg. The distal seal of the device was placed against the sclera at the pars plana, approximately 6 mm posterior of the limbus. The device was angled approximately 30 degrees from the surface of the globe with the needle bevel opening directed posteriorly. The device was advanced, allowing the needle tip to penetrate the distal seal and enter the scleral tissues. When the needle tip reached the suprachoroidal space, the flexible cannula advanced under the force of the force element compression spring. After deployment, the fluorescein solution was injected through the device. The device was withdrawn and set aside. A scleral cut-down was made from the area of needle penetration and extended posteriorly toward the target region for the distal end of the deployed cannula. The dissection revealed the fluorescein solution in the suprachoroidal space.

Example 3

Low Sealing Force Tissue Interface

Tissue interfaces were fabricated in a manner similar to those described in Example 1. Two different outer diameters of tissue interface were fabricated: 1.75 mm diameter and 2.50 mm diameter. Samples of each diameter tissue interface were fabricated using four different durometers of liquid silicone elastomer, Shore 10A, 30A, 50A and 70A.

An experimental set-up was prepared to determine the sealing force of the various samples of the tissue interface. A segment of PEEK tubing 8.3 mm long was placed over a 27 gauge×13 mm thin walled hypodermic needle to serve as a stop so as not to allow the tissue seals to travel proximally during the test. A tissue seal being tested was then placed over the needle tip. The length of the PEEK tubing was sized so as to allow approximately one-half of the needle bevel section to protrude through the tissue interface distal surface. A test surface was used which consisted of a silicone elastomer pad with a durometer of Shore 50A and 3.2 mm thick. The needle was mounted to a tee-fitting which in turn was mounted on the shaft of a digital force gauge with a 250N capacity mounted on a motorized test stand. The side leg of the tee-fitting was attached to a length of tubing and then to a Luer fitting and a three-way valve. A 10 cc syringe filled with water was attached to the valve. The syringe was held vertically using a ring stand. Tests were conducted using two different constant pressures which were generated by applying fixed weights of 1030 and 1656 grams respectively to the finger flange of the syringe plunger. The inside of the syringe had a cross-sectional area of $1.64 \times 10^{-4}$ m² which corresponded to fluid pressures of $6.18 \times 10^4$ Pa and $9.93 \times 10^4$ Pa respectively.

Figure 12:
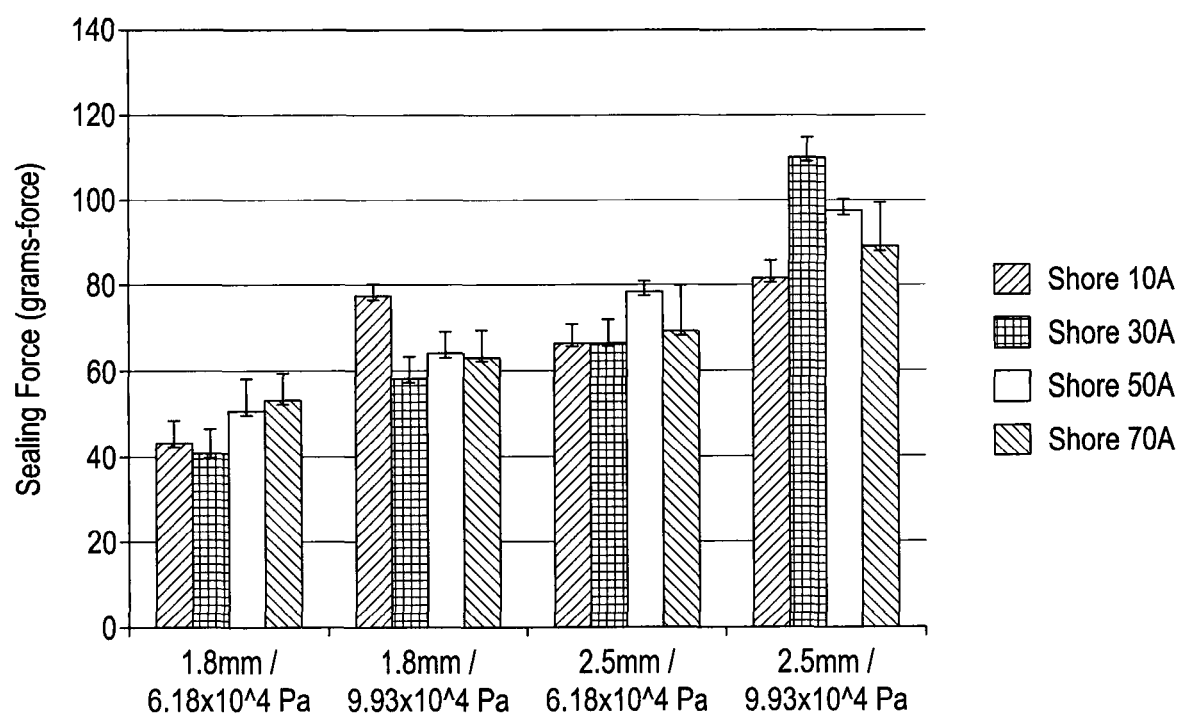
FIG. 12 is a graph of test results of the tissue interface minimum sealing force.

To perform a test, the needle tip was traversed down until the tissue interface was close to touching the silicone test pad. The test stand motor was jogged downward until approximately 30 grams-force of pressure was being applied to the tissue interface. The three-way valve was opened and the periphery of the tissue interface observed for water leakage. The valve was closed and then the needle was moved downward until approximately 35 grams-force of pressure was being applied. The valve was opened and the tissue interface observed for leakage. The tissue interface pressure on the test pad was increased in 5 gram-force increments in this manner until no leakage was observed, e.g. a seal was achieved and the force was recorded. The test was repeated with the second syringe pressure weight. The testing was performed on the two different tissue interface diameters and the four different durometers (Table 1 and FIG. 12). Two samples of each tissue interface were tested three times each for a total of six data points for each test condition. The silicone test pad was moved after each test so that each needle penetration was at a new site. FIG. 12 shows a tissue interface minimum sealing force graph grouped by diameter & fluid pressure, as a function of durometer. Table 1 shows the minimum Sealing Force in Gram-Force for Tissue Interface Test Samples (Average and Standard Deviation) grouped by Tissue Interface Diameter and Fluid Pressure, as a Function of Durometer.

TABLE 1

| Durometer | 1.8 mm Diameter $6.18 \times 10^4$ Pa | 1.8 mm Diameter $9.93 \times 10^4$ Pa | 2.5 mm Diameter $6.18 \times 10^4$ Pa | 2.5 mm Diameter $9.93 \times 10^4$ Pa |
|---|---|---|---|---|
| 10 | 43.3 ± 5.2 | 77.5 ± 2.7 | 66.7 ± 4.1 | 81.7 ± 4.1 |
| 30 | 40.8 ± 5.8 | 58.3 ± 5.2 | 66.7 ± 5.2 | 110.0 ± 4.5 |
| 50 | 50.8 ± 7.4 | 64.2 ± 4.9 | 78.3 ± 2.6 | 97.5 ± 2.7 |
| 70 | 53.3 ± 6.1 | 63.3 ± 6.1 | 69.2 ± 10.7 | 89.2 ± 10.2 |

Example 4

Semisolid Drug Composition

A semisolid drug composition was prepared. A 1.5 wt % of polyethylene oxide (PolyOx WSR-303) of 7 million Daltons average molecular weight was dispersed in deionized water. Dexamethasone crystals with an average diameter of approximately 2 microns were mixed into the polyethylene oxide dispersion at a concentration of 8 wt %. The semisolid composition was opaque due to the dispersed dexamethasone crystals.

A cannulation device according to Example 2 was fabricated to inject the semisolid composition into the suprachoroidal space of an eye. The cannula was configured with a 10 mm deployed length.

An enucleated porcine eye was prepared by infusion to 17 mm Hg. The distal tip of the cannulation device was placed on the pars plana region of the eye and advanced into the eye with the bevel directed posteriorly. The self-actuated deployment of the cannula was observed to occur once the tip of the needle reached the appropriate depth to access the suprachoroidal space. Approximately one hundred microliters of the semisolid drug composition were administered into the proximal end of the cannula through the female Luer lock connector. After administration, dissection of the sclera from the needle penetration site to the area 10 mm from the needle penetration site in the posterior direction of cannulation was performed. Dissection to the suprachoroidal space revealed the semisolid composition in the posterior region of the suprachoroidal space. No perforation into the vitreous cavity was observed.

The invention claimed is:

1. A cannulation device for administering an active agent containing composition to an eye comprising:
    an elongated body with a hollow needle at a distal end;
    a cannula comprising an elongated tubular element with an atraumatic distal tip, where at least a portion of the tubular element is contained in a lumen of the needle prior to deployment;
    a force element that provides a deployment force to advance the tubular element through the needle lumen;
    a mechanical coupling element from the force element to the tubular element;
    either:
        i) a reservoir to contain an active agent containing composition for administration in communication with the proximal end of the tubular element; or
        ii) a connector or an injection port in communication with the proximal end of the tubular element for delivery of an active agent containing composition; and
    a mechanism for activation of the force element prior to or simultaneous with placement of the distal tip of the needle into the eye;
    wherein:
        the deployment force from the force element acts to advance the tubular element out from the distal end of the needle into the suprachoroidal space or supraciliary space.

2. The device of claim 1 additionally comprising
    a distal element attached to the distal end of the device thereby sealing or blocking the needle lumen from advancement of the tubular element out of the needle while under the deployment force;
    the distal element comprises a distal seal, and wherein the distal seal acts as a tissue interface and is penetrable by a distal tip of the needle by an application of pressure on the surface of an eye with the distal end of the device;
    the penetrated distal element becomes slidable on the needle to allow advancement of the needle into tissue; and
    the penetrated distal seal opens a path for advancement of the tubular element from the distal end of the needle.

3. The device of claim 2, additionally comprising a collapsible element between the body of the device and the distal element, wherein the collapsible element is configured to prevent distal movement of the distal element due to the deployment force.

4. The device of claim 3 wherein the collapsible element comprises elongated struts.

5. The device of claim 3 wherein the collapsible element comprises nitinol or polyimide.

6. The device of claim 3, wherein the collapsible element is configured to provide a forward directed force on the distal element during penetration of the distal seal by the distal tip of the needle.

7. The device of claim 6 where the forward directed force is in the range of 40 to 82 gram force.

8. The device of claim 6 wherein the collapsible element is configured to provide a constant force after an initial force wherein the initial force is applied during the first 0.5 mm of travel of the distal element proximally along the needle.

9. The device of claim 2, wherein the distal seal acts as a tissue interface, where the distal seal comprises an elastomer with a hardness of 10 to 30 Shore A.

10. The device of claim 2, wherein the distal seal is mounted on a tubular distal housing.

11. A method for treatment of an ocular disease or condition by delivery of a liquid or semisolid material to the suprachoroidal space or supraciliary space comprising activating the force element of the cannulation device of claim 2 to provide a deployment force on the cannula, placing the distal seal of the device on a surface of the eye and advancing the needle of the device through the distal seal to open a flow path from the distal tip of the needle, advancing the needle into tissue until the cannula is deployed and delivering the material to the space.

12. The method of claim 11 where the material for administration comprises a steroid, non-steroidal anti-inflammatory agent, antibiotic, VEGF inhibitor, anti-TNF alpha agent, mTOR inhibitor, cell therapy, anti-hypertensive agent, antihistamine, aminosterol, neuroprotective agent or nucleic acid based therapeutic.

13. The method of claim 11 wherein the ocular disease or condition comprises inflammation, infection, macular degeneration, retinal degeneration, neovascularization, proliferative vitreoretinopathy, glaucoma or edema.

14. A method for treatment of an ocular disease or condition by injection of a solid or semisolid material to the suprachoroidal space or supraciliary space comprising filling the cannulation device of claim 2 with the material, activating the force element of said cannulation device to provide a deployment force on the cannula, placing the tissue interface of the device on the surface of the eye and advancing the needle of the device through the distal seal to open a path for delivery of the cannula from the distal tip of the needle, advancing the needle into tissue until the cannula is deployed and delivering the material to the space.

15. A method for injection of a material into the suprachoroidal space or supraciliary space using the device of claim 2 wherein the cannula is subjected to a deployment force by the force element prior to introduction of the distal tip of the device into tissues wherein advancement of the needle through the distal seal opens a path for delivery of the cannula from the distal tip, thereby enabling single-handed use of the device without actuation of injection by a valve or trigger on the body of the cannulation device.

16. The device of claim 1, wherein the force element is a spring which is mechanically coupled to a plunger.

17. The device of claim 1, wherein the force element is a pressurized gas.

18. The device of claim 1, additionally comprising a damping mechanism.

19. The cannulation device of claim 1, wherein the deployment force is activated by a mechanism to compress the force element from the exterior of the device.

20. The cannulation device of claim 1, wherein the force element is constrained prior to use and the deployment force is activated by mechanically releasing the constrained force element.

21. The cannulation device of claim 1, for delivery of an active agent containing composition to the suprachoroidal space or supraciliary space with an effective full needle length of 1 to 4 mm.

22. The cannulation device of claim 1, for delivery of an active agent containing composition to the vitreous cavity with an effective full needle length of 10 to 15 mm.

23. The cannulation device of claim 1, for delivery of an active agent containing composition to the subconjunctival space with an effective full needle length of 0.35 to 2 mm.

24. The device of claim 1 wherein the needle comprises a curved distal tip to direct the tubular element at an angle from the long axis of the needle toward the posterior region of the eye.

25. The device of claim 1 wherein the needle comprises an inner deflecting element in the lumen of the needle at a needle bevel to direct the tubular element at an angle from the long axis of the needle toward the posterior region of the eye.

26. The device of claim 1, wherein when the device comprises the reservoir, the reservoir contains an active agent containing composition for administration;
   wherein the composition is a semi-solid composition comprising a plurality of drug containing particles and an excipient;
   wherein the drug is selected from the group consisting of a steroid, a non-steroidal anti-inflammatory agent, a VEGF inhibitor, an anti-TNF alpha agent, an mTOR inhibitor, a cell therapy, a nucleic acid based therapeutic, and/or a neuroprotectant.

27. A cannulation device for administering an active agent containing composition to an eye comprising:
   an elongated body with a hollow needle at a distal end;
   a cannula comprising an elongated tubular element with an atraumatic distal tip, where at least a portion of the tubular element is contained in a lumen of the needle prior to deployment
   a force element that provides a deployment force to advance the tubular element through the needle lumen;
   a mechanical coupling element from the force element to the tubular element either:
      i) a reservoir to contain an active agent containing composition for administration in communication with the proximal end of the tubular element; or
      ii) a connector or an injection port in communication with the proximal end of the tubular element for delivery of an active agent containing composition;
   a mechanism for activation of the force element prior to or simultaneous with placement of the distal tip of the needle into the eye; and
   a distal element attached to the distal end of the device thereby sealing or blocking the needle lumen from advancement of the tubular element out of the needle while under the deployment force;
wherein:
   the deployment force from the force element acts to advance the tubular element out from the distal end of the needle into the suprachoroidal space or supraciliary space;
   the distal element comprises a distal seal, and wherein the distal seal acts as a tissue interface and is penetrable by a distal tip of the needle by the application of pressure on the surface of an eye with the distal end of the device;
   the penetrated distal element becomes slidable on the needle to allow advancement of the needle into tissue;
   the penetrated distal seal opens a path for advancement of the tubular element from the distal end of the needle; and
   the distal seal comprises deformable protrusions that extend into the lumen at the distal end of the needle or that extend into a distal projection of the lumen from the distal end that would be sufficient to prevent deployment of the tubular element under the deployment force.

* * * * *